(12) United States Patent
Libbus

(10) Patent No.: US 7,706,884 B2
(45) Date of Patent: Apr. 27, 2010

(54) BAROREFLEX STIMULATION SYNCHRONIZED TO CIRCADIAN RHYTHM

(75) Inventor: Imad Libbus, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 351 days.

(21) Appl. No.: 10/746,844

(22) Filed: Dec. 24, 2003

(65) Prior Publication Data

US 2005/0149130 A1 Jul. 7, 2005

(51) Int. Cl.
A61N 1/36 (2006.01)
(52) U.S. Cl. ...................................................... 607/44
(58) Field of Classification Search ................... 607/44
See application file for complete search history.

(56) References Cited

U.S. PATENT DOCUMENTS

| | | | |
|---|---|---|---|
| 3,421,511 A * | 1/1969 | Wingrove et al. | 607/118 |
| 3,522,811 A * | 8/1970 | Wingrove et al. | 607/27 |
| 3,650,277 A | 3/1972 | Sjostrand et al. | |
| 4,770,177 A | 9/1988 | Schroeppel | |
| 4,791,931 A | 12/1988 | Slate | 128/419 |
| 4,936,304 A | 6/1990 | Kresh et al. | |
| 5,052,388 A | 10/1991 | Sivula et al. | |
| 5,111,815 A | 5/1992 | Mower | 128/419 |
| 5,190,035 A | 3/1993 | Salo et al. | 128/419 |
| 5,199,428 A | 4/1993 | Obel et al. | 128/419 C |
| 5,203,326 A | 4/1993 | Collins | 128/419 PG |
| 5,243,980 A | 9/1993 | Mehra | 607/6 |
| 5,318,592 A | 6/1994 | Schaldach | 607/5 |
| 5,330,507 A | 7/1994 | Schwartz | 607/14 |
| 5,334,221 A | 8/1994 | Bardy | |
| 5,356,425 A | 10/1994 | Bardy et al. | 607/14 |
| 5,374,282 A | 12/1994 | Nichols et al. | |
| 5,411,531 A | 5/1995 | Hill et al. | 607/14 |
| 5,437,285 A | 8/1995 | Verrier et al. | 128/702 |
| 5,507,784 A | 4/1996 | Hill et al. | 607/14 |
| 5,522,854 A | 6/1996 | Ideker et al. | 607/6 |
| 5,562,711 A | 10/1996 | Yerich et al. | |
| 5,578,061 A | 11/1996 | Stroetmann et al. | 607/4 |
| 5,658,318 A | 8/1997 | Stroetmann et al. | 607/6 |
| 5,662,689 A | 9/1997 | Elsberry et al. | |
| 5,690,681 A | 11/1997 | Geddes et al. | 607/2 |

(Continued)

FOREIGN PATENT DOCUMENTS

EP 0547734 A2 6/1993

(Continued)

OTHER PUBLICATIONS

"http://www.cardioconsult.com/Anatomy/", http://www.cardioconsult.com/Anatomy/, (2003),4.

(Continued)

*Primary Examiner*—Carl H. Layno
*Assistant Examiner*—Tammie K Heller
(74) *Attorney, Agent, or Firm*—Schwegman, Lundberg & Woessner, P.A.

(57) ABSTRACT

An aspect relates to a baroreflex stimulator. An embodiment of the stimulator comprises a pulse generator to provide a baroreflex stimulation signal through an electrode, and a modulator to modulate the baroreflex stimulation signal based on a circadian rhythm template.

28 Claims, 22 Drawing Sheets

U.S. PATENT DOCUMENTS

| | | | |
|---|---|---|---|
| 5,700,282 A | 12/1997 | Zabara | 607/9 |
| 5,707,400 A * | 1/1998 | Terry et al. | 607/44 |
| 5,916,239 A | 6/1999 | Geddes et al. | 607/14 |
| 6,006,134 A * | 12/1999 | Hill et al. | 607/9 |
| 6,035,233 A | 3/2000 | Schroeppel et al. | |
| 6,058,331 A | 5/2000 | King | 607/62 |
| 6,073,048 A * | 6/2000 | Kieval et al. | 607/17 |
| 6,134,470 A | 10/2000 | Hartlaub | 607/14 |
| 6,144,878 A | 11/2000 | Schroeppel et al. | |
| 6,161,042 A | 12/2000 | Hartley et al. | 607/20 |
| 6,178,349 B1 | 1/2001 | Kieval | 607/118 |
| 6,181,966 B1 | 1/2001 | Nigam | 607/4 |
| 6,240,314 B1 | 5/2001 | Plicchi et al. | 607/14 |
| 6,240,316 B1 | 5/2001 | Richmond et al. | |
| 6,266,564 B1 | 7/2001 | Hill et al. | |
| 6,272,377 B1 | 8/2001 | Sweeney et al. | 600/515 |
| 6,285,907 B1 | 9/2001 | Kramer et al. | |
| 6,292,695 B1 | 9/2001 | Webster, Jr. et al. | 607/14 |
| 6,292,703 B1 | 9/2001 | Meier et al. | |
| 6,371,922 B1 | 4/2002 | Baumann et al. | 600/485 |
| 6,400,982 B2 | 6/2002 | Sweeney et al. | 600/515 |
| 6,411,845 B1 | 6/2002 | Mower | |
| 6,421,557 B1 | 7/2002 | Meyer | 600/516 |
| 6,449,507 B1 | 9/2002 | Hill et al. | 607/9 |
| 6,473,644 B1 | 10/2002 | Terry, Jr. et al. | 607/2 |
| 6,487,450 B1 | 11/2002 | Chen | 607/9 |
| 6,493,585 B2 | 12/2002 | Plicchi et al. | 607/14 |
| 6,511,500 B1 | 1/2003 | Rahme | 607/1 |
| 6,522,926 B1 | 2/2003 | Kieval et al. | 607/44 |
| 6,532,388 B1 | 3/2003 | Hill et al. | 607/2 |
| 6,542,774 B2 | 4/2003 | Hill et al. | 607/9 |
| 6,564,096 B2 | 5/2003 | Mest | 607/14 |
| 6,611,713 B2 | 8/2003 | Schauerte | 607/14 |
| 6,622,041 B2 | 9/2003 | Terry, Jr. et al. | 607/9 |
| 6,628,987 B1 | 9/2003 | Hill et al. | |
| 6,788,970 B1 | 9/2004 | Park et al. | |
| 6,934,583 B2 | 8/2005 | Weinberg et al. | |
| 6,985,774 B2 | 1/2006 | Kieval et al. | |
| 7,092,755 B2 | 8/2006 | Florio | |
| 7,123,959 B2 | 10/2006 | Cates | |
| 7,123,967 B2 | 10/2006 | Weinberg | |
| 7,139,607 B1 | 11/2006 | Shelchuk | |
| 7,155,284 B1 * | 12/2006 | Whitehurst et al. | 607/44 |
| 7,158,832 B2 | 1/2007 | Kieval et al. | |
| 7,194,313 B2 | 3/2007 | Libbus | |
| 7,245,967 B1 | 7/2007 | Shelchuk | |
| 7,260,431 B2 | 8/2007 | Libbus et al. | |
| 7,277,761 B2 | 10/2007 | Shelchuk | |
| 7,299,086 B2 | 11/2007 | McCabe et al. | |
| 7,321,793 B2 | 1/2008 | Ben Ezra et al. | |
| 7,333,854 B1 | 2/2008 | Brewer et al. | |
| 7,403,819 B1 | 7/2008 | Shelchuk et al. | |
| 7,460,906 B2 | 12/2008 | Libbus | |
| 7,486,991 B2 | 2/2009 | Libbus et al. | |
| 7,493,161 B2 | 2/2009 | Libbus et al. | |
| 7,499,748 B2 | 3/2009 | Moffitt et al. | |
| 7,509,166 B2 | 3/2009 | Libbus | |
| 7,542,800 B2 | 6/2009 | Libbus et al. | |
| 7,548,780 B2 | 6/2009 | Libbus et al. | |
| 7,551,958 B2 | 6/2009 | Libbus et al. | |
| 7,555,341 B2 | 6/2009 | Moffitt et al. | |
| 7,561,923 B2 | 7/2009 | Libbus et al. | |
| 7,584,004 B2 | 9/2009 | Caparso et al. | |
| 2001/0020136 A1 | 9/2001 | Sweeney et al. | |
| 2002/0004670 A1 | 1/2002 | Florio et al. | |
| 2002/0026221 A1 | 2/2002 | Hill et al. | 607/9 |
| 2002/0026222 A1 | 2/2002 | Schauerte et al. | 607/14 |
| 2002/0058877 A1 | 5/2002 | Baumann et al. | 600/485 |
| 2002/0072776 A1 | 6/2002 | Osorio et al. | |
| 2002/0077670 A1 | 6/2002 | Archer et al. | |
| 2002/0091415 A1 | 7/2002 | Lovett et al. | |
| 2002/0107553 A1 | 8/2002 | Hill et al. | 607/18 |
| 2002/0120304 A1 | 8/2002 | Mest | 607/14 |
| 2002/0143369 A1 | 10/2002 | Hill et al. | 607/9 |
| 2002/0161410 A1 | 10/2002 | Kramer et al. | |
| 2002/0165586 A1 | 11/2002 | Hill et al. | 607/9 |
| 2002/0183237 A1 | 12/2002 | Puskas | |
| 2002/0183793 A1 | 12/2002 | Struble et al. | |
| 2002/0198570 A1 | 12/2002 | Puskas | |
| 2003/0003052 A1 | 1/2003 | Hampton | 424/9.2 |
| 2003/0004549 A1 | 1/2003 | Hill et al. | 607/9 |
| 2003/0023279 A1 | 1/2003 | Spinelli et al. | |
| 2003/0036773 A1 | 2/2003 | Whitehurst et al. | |
| 2003/0040774 A1 | 2/2003 | Terry et al. | |
| 2003/0045909 A1 | 3/2003 | Gross et al. | 607/9 |
| 2003/0045914 A1 | 3/2003 | Cohen et al. | |
| 2003/0060848 A1 | 3/2003 | Kieval et al. | 607/2 |
| 2003/0060857 A1 | 3/2003 | Perrson et al. | 607/44 |
| 2003/0060858 A1 | 3/2003 | Kieval et al. | 607/44 |
| 2003/0074039 A1 | 4/2003 | Puskas | |
| 2003/0078623 A1 | 4/2003 | Weinberg et al. | 607/9 |
| 2003/0078629 A1 | 4/2003 | Chen | 607/9 |
| 2003/0100924 A1 | 5/2003 | Foreman et al. | 607/9 |
| 2003/0105493 A1 | 6/2003 | Salo | |
| 2003/0149450 A1 | 8/2003 | Mayberg | 607/3 |
| 2003/0181951 A1 | 9/2003 | Cates | |
| 2003/0195578 A1 | 10/2003 | Perron et al. | |
| 2003/0212440 A1 | 11/2003 | Boveja | 607/46 |
| 2003/0212445 A1 | 11/2003 | Weinberg | |
| 2003/0216792 A1 | 11/2003 | Levin et al. | |
| 2003/0229380 A1 * | 12/2003 | Adams et al. | 607/9 |
| 2003/0236558 A1 | 12/2003 | Whitehurst et al. | |
| 2004/0010303 A1 | 1/2004 | Bolea | |
| 2004/0019364 A1 | 1/2004 | Kieval et al. | |
| 2004/0049235 A1 | 3/2004 | Deno et al. | |
| 2004/0054381 A1 | 3/2004 | Pastore et al. | |
| 2004/0088015 A1 | 5/2004 | Casavant et al. | |
| 2004/0116970 A1 | 6/2004 | Girouard et al. | |
| 2004/0172074 A1 | 9/2004 | Yoshihito | |
| 2004/0193231 A1 | 9/2004 | David et al. | |
| 2004/0199210 A1 | 10/2004 | Shelchuk | |
| 2004/0215289 A1 | 10/2004 | Fukui | |
| 2004/0220621 A1 | 11/2004 | Zhou et al. | |
| 2004/0249416 A1 | 12/2004 | Yun et al. | |
| 2004/0254616 A1 | 12/2004 | Rossing et al. | |
| 2005/0059897 A1 | 3/2005 | Snell et al. | |
| 2005/0065555 A1 | 3/2005 | Er | |
| 2005/0065575 A1 | 3/2005 | Dobak | |
| 2005/0085864 A1 | 4/2005 | Schulman et al. | |
| 2005/0096705 A1 | 5/2005 | Pastore et al. | |
| 2005/0131467 A1 | 6/2005 | Boveja | |
| 2005/0143779 A1 | 6/2005 | Libbus | |
| 2005/0143785 A1 | 6/2005 | Libbus | |
| 2005/0143787 A1 | 6/2005 | Boveja et al. | |
| 2005/0149126 A1 | 7/2005 | Libbus | |
| 2005/0149127 A1 | 7/2005 | Libbus | |
| 2005/0149128 A1 | 7/2005 | Heil, Jr. et al. | |
| 2005/0149129 A1 | 7/2005 | Libbus et al. | |
| 2005/0149130 A1 | 7/2005 | Libbus | |
| 2005/0149131 A1 | 7/2005 | Libbus et al. | |
| 2005/0149132 A1 | 7/2005 | Libbus | |
| 2005/0149133 A1 | 7/2005 | Libbus et al. | |
| 2005/0149143 A1 | 7/2005 | Libbus et al. | |
| 2005/0149155 A1 | 7/2005 | Scheiner et al. | |
| 2005/0149156 A1 | 7/2005 | Libbus et al. | |
| 2005/0154418 A1 | 7/2005 | Kieval et al. | |
| 2005/0197675 A1 | 9/2005 | David et al. | |
| 2006/0074453 A1 | 4/2006 | Kieval et al. | |
| 2006/0079945 A1 | 4/2006 | Libbus | |
| 2006/0089678 A1 * | 4/2006 | Shalev | 607/23 |
| 2006/0106428 A1 | 5/2006 | Libbus et al. | |
| 2006/0106429 A1 | 5/2006 | Libbus et al. | |
| 2006/0116737 A1 | 6/2006 | Libbus | |
| 2006/0122675 A1 | 6/2006 | Libbus et al. | |

| | | |
|---|---|---|
| 2006/0217772 A1 | 9/2006 | Libbus et al. |
| 2006/0253156 A1 | 11/2006 | Pastore et al. |
| 2006/0259107 A1 | 11/2006 | Caparso et al. |
| 2006/0271115 A1 | 11/2006 | Ben-Ezra et al. |
| 2006/0271118 A1 | 11/2006 | Libbus et al. |
| 2006/0282131 A1 | 12/2006 | Caparso et al. |
| 2007/0021790 A1 | 1/2007 | Kieval et al. |
| 2007/0021792 A1 | 1/2007 | Kieval et al. |
| 2007/0021796 A1 | 1/2007 | Kieval et al. |
| 2007/0021797 A1* | 1/2007 | Kieval et al. ........... 607/44 |
| 2007/0021798 A1 | 1/2007 | Kieval et al. |
| 2007/0021799 A1 | 1/2007 | Kieval et al. |
| 2007/0034261 A1 | 2/2007 | Eichler |
| 2007/0038259 A1* | 2/2007 | Kieval et al. ........... 607/44 |
| 2007/0038260 A1 | 2/2007 | Kieval et al. |
| 2007/0038261 A1 | 2/2007 | Kieval et al. |
| 2007/0038262 A1 | 2/2007 | Kieval et al. |
| 2007/0060972 A1 | 3/2007 | Kieval et al. |
| 2007/0068260 A1 | 3/2007 | Hong et al. |
| 2007/0093875 A1 | 4/2007 | Chavan et al. |
| 2007/0142864 A1 | 6/2007 | Libbus et al. |
| 2007/0167984 A1 | 7/2007 | Kieval et al. |
| 2007/0191904 A1 | 8/2007 | Libbus et al. |
| 2008/0021507 A1 | 1/2008 | Libbus et al. |
| 2008/0125843 A1 | 5/2008 | Ben-David et al. |
| 2008/0167694 A1 | 7/2008 | Bolea et al. |
| 2008/0228238 A1 | 9/2008 | Libbus |
| 2009/0048641 A1 | 2/2009 | Libbus |
| 2009/0143834 A1 | 6/2009 | Libbus |
| 2009/0143838 A1 | 6/2009 | Libbus et al. |

FOREIGN PATENT DOCUMENTS

| | | |
|---|---|---|
| EP | 1486232 A2 | 12/2004 |
| EP | 1541193 A1 | 6/2005 |
| WO | WO-0124876 A1 | 4/2001 |
| WO | WO-0176689 A2 | 10/2001 |
| WO | WO-0226318 A1 | 4/2002 |
| WO | WO-0234327 A2 | 5/2002 |
| WO | WO-02085448 A2 | 10/2002 |
| WO | WO-03011388 A2 | 2/2003 |
| WO | WO-03041559 A2 | 5/2003 |
| WO | WO-03076008 A1 | 9/2003 |
| WO | WO-03082080 A2 | 10/2003 |
| WO | WO-03082080 A3 | 10/2003 |
| WO | WO-03099373 A2 | 12/2003 |
| WO | WO-03099377 A1 | 12/2003 |
| WO | WO-2004012814 A1 | 2/2004 |
| WO | WO-2004084990 A1 | 10/2004 |
| WO | WO-2004084993 A1 | 10/2004 |
| WO | WO-2004103455 A2 | 12/2004 |
| WO | WO-2004105870 A1 | 12/2004 |
| WO | WO-2004110549 A2 | 12/2004 |
| WO | WO-2005018739 A1 | 3/2005 |
| WO | WO-2005042091 A1 | 5/2005 |
| WO | WO-2005053788 A1 | 6/2005 |
| WO | WO-2005063332 A1 | 7/2005 |
| WO | WO-2005065771 A1 | 7/2005 |
| WO | WO-2006031331 A1 | 3/2006 |
| WO | WO-2008063396 A1 | 5/2008 |

OTHER PUBLICATIONS

American Heart Association, "Hypertension Population Statistics", (2002).
Andersen, H, "Long-term follow-up of patients from a randomised trial of atrial versus ventricular pacing for sick-sinus syndrome", *Lancet*, 350(9086), (Oct. 25, 1997),1210-6.
Benchimol, A, "Cardiac hemodynamics during stimulation of the right atrium, right ventricle, and left ventricle in normal and abnormal hearts", *Circulation*, 33(6), (Jun. 1966),933-44.
Bevan, J A., et al., "Postganglionic sympathetic delay in vascular smooth muscle", *Journal of Pharmacology & Experimental Therapeutics*, 152(2), (May 1966),221-30.
Bevan, J A., et al., "Sympathetic nerve-free vascular muscle", *Journal of Pharmacology & Experimental Therapeutics*, 157(1), (Jul. 1967),117-24.
Bilgutay, A M., et al., "A new concept in the treatment of hypertension utilizing an implantable electronic device: "Baropacer"", *Trans Am Soc Artif Intern Organs.*, 10, (1964),387-95.
Bilgutay, A M., et al., "Vagal tuning for the control of supraventricular arrhythmias", *Surgical Forum*, 16, (1965),151-3.
Bilgutay, Aydin M., "Vagal tuning. A new concept in the treatment of supraventricular arrhythmias, angina pectoris, and heart failure", *Journal of Thoracic and Cardiovascular Surgery*, 56(1), (Jul. 1968),71-82.
Borst, C, et al., "Optimal frequency of carotid sinus nerve stimulation in treatment of angina pectoris", *Cardiovascular Research*, 8(5), (Sep. 1974),674-80.
Braunwald, E, et al., "Carotid sinus nerve stimulation in the treatment of angina pectoris and supraventricular tachycardia", *California Medicine*, 112(3), (Mar. 1970),41-50.
Braunwald, E, et al., "Relief of angina pectoris by electrical stimulation of the carotid-sinus nerves", *New England Journal of Medicine*, 277(24), (Dec. 14, 1967),1278-83.
Coleridge, J C., et al., "Relationship between pulmonary arterial pressure and impulse activity in pulmonary arterial baroreceptor fibres", *Journal of Physiology*, 158, (Sep. 1961),197-205.
Coleridge, J C., et al., "The distribution, connexions and histology of baroreceptors in the pulmonary artery, with some observations on the sensory innervation of the ductus arteriosus", *Journal of Physiology*, 156, (May 1961),591-602.
Cooper, T B., et al., "Neural effects on sinus rate and atrioventricular conduction produced by electrical stimulation from a transvenous electrode catheter in the canine right pulmonary artery", *Circulation Research*, 46(1), (Jan. 1980),48-57.
Courtice, G P., et al., "Effect of frequency and impulse pattern on the non-cholinergic cardiac response to vagal stimulation in the toad, Bufo marinus", *Journal of the Autonomic Nervous System*, 48(3), (Aug. 1994),267-72.
Dart Jr., C H., et al., "Carotid sinus nerve stimulation treatment of angina refractory to other surgical procedures", *Annals of Thoracic Surgery*, 11(4), (Apr. 1971),348-59.
De Landsheere, D, et al., "Effect of spinal cord stimulation on regional myocardial perfusion assessed by positron emission tomography", *American Journal of Cardiology*, 69(14), (May 1, 1991),1143-9.
Dunning, Arend J., "Electrostimulation of the Carotid Sinus Nerve in Angina Pectoris", *University Department of Medicine, Binnenasthuis, Amsterdam*; Printed by Royal VanGorcum, Assen, Netherlands, (1971),1-92.
Epstein, S E., et al., "Treatment of angina pectoris by electrical stimulation of the carotid-sinus nerves", *New England Journal of Medicine*, 280(18), (May 1, 1969),971-8.
Farrehi, C, "Stimulation of the carotide sinus nerve in treatment of angina pectoris", *American Heart Journal*, 80(6), (Dec. 1970),759-65.
Feliciano, L, et al., "Vagal nerve stimulation releases vasoactive intestinal peptide which significantly increases coronary artery blood flow", *Cardiovascular Research*, 40(1), (Oct. 1998),45-55.
Fromer M, et al., "Ultrarapid subthreshold stimulation for termination of atrioventricular node reentrant tachycardia", *Journal of the American College of Cardiology*, 20(4), (Oct. 1992),879-83.
Grassi, Guido, et al., "Baroreflex and non-baroreflex modulation of vagal cardiac control after myocardial infarction", *Am J Cardiol.*, 84(5), (Sep. 1, 1999),525-9.
Griffith, Lawrence S., et al., "Electrical Stimulation of the Carotid Sinus Nerve in Normotensive and Renal Hypertensive and Renal Hypertensive Dogs", *Circulation*, 28, (Jul.-Dec. 1963),730.
Heil, Jr., Ronald W., et al., "Baroreflex Stimulation System to Reduce Hypertension", U.S. Appl. No. 10/746,134, filed Dec. 24, 2003, 78 pgs.
Henning, R J., "Effects of autonomic nerve stimulation, asynchrony, and load on dP/dtmax and on dP/dtmin", *American Journal of Physiology*, 260(4 Pt 2), (Apr. 1991),H1290-8.

Henning, R J., et al., "Vagal nerve stimulation increases right ventricular contraction and relaxation and heart rate", *Cardiovascular Research*, 32(5), (Nov. 1996),846-53.

Henning, R J., et al., "Vagal stimulation attenuates sympathetic enhancement of left ventricular function", *American Journal of Physiology*, 258(5 Pt 2), (May 1990),H1470-5.

Hood Jr., W B., et al., "Asynchronous contraction due to late systolic bulging at left ventricular pacing sites", *American Journal of Physiology*, 217(1), (Jul. 1969),215-21.

Ishise, H, "Time course of sympathovagal imbalance and left ventricular dysfunction in conscious dogs with heart failure", *Journal of Applied Physiology*, 84(4), (Apr. 1998),1234-41.

Jessurun, G A., et al., "Coronary blood flow dynamics during transcutaneous electrical nerve stimulation for stable angina pectoris associated with severe narrowing of one major coronary artery", *American Journal of Cardiology*, 82(8), erratum appears in Am J Cardiol Feb. 15, 1999;83(4):642,(Oct. 15, 1998),921-6.

Kandel, Eric R., et al., "Part VII: Arousal, Emotion, and Behavioral Homeostasis", *In: Principles of neural science*, New York : McGraw-Hill, Health Professions Division,(2000),966-969.

Karpawich, P P., et al., "Altered cardiac histology following apical right ventricular pacing in patients with congenital atrioventricular block", *Pacing Clin Electrophysiol.*, 22(9), (Sep. 1999),1372-7.

Leclercq, C, et al., "Hemodynamic importance of preserving the normal sequence of ventricular activation in permanent cardiac pacing", *Am Heart J.*, 129(6), (Jun. 1995),1133-41.

Libbus, Imad, "Automatic Baroreflex Modulation Based on Cardiac Activity", U.S. Appl. No. 10/746,846, filed Dec. 24, 2003, 83 pgs.

Libbus, Imad, "Automatic Baroreflex Modulation Responsive to Adverse Event", U.S. Appl. No. 10/745,925, filed Dec. 24, 2003, 81 pgs.

Libbus, Imad, et al., "Baropacing and Cardiac Pacing to Control Output", U.S. Appl. No. 10/746,135, filed Dec. 24, 2003, 79 pgs.

Libbus, Imad, et al., "Baroreflex Modulation to Gradually Decrease Blood Pressure", U.S. Appl. No. 10/746,845, filed Dec. 24, 2003, 83 pgs.

Libbus, Imad, "Baroreflex Stimulation to Treat Acute Myocardial Infarction", U.S. Appl. No. 10/745,920, filed Dec. 24, 2003, 78 pgs.

Libbus, Imad, "Baroreflex Stimulator With Integrated Pressure Sensor", U.S. Appl. No. 10/745,921, filed Dec. 24, 2003, 80 pgs.

Libbus, Imad, et al., "Lead for Stimulating the Baroreceptors in the Pulmonary Artery", U.S. Appl. No. 10/746,861, filed Dec. 24, 2003, 21 pgs.

Libbus, Imad, et al., "Sensing With Compensation for Neural Stimulator", U.S. Appl. No. 10/746,847, filed Dec. 24, 2003, 79 pgs.

Mannheimer, C, et al., "Epidural spinal electrical stimulation in severe angina pectoris", *British Heart Journal*, 59(1), (Jan. 1988),56-61.

Mannheimer, C, et al., "Transcutaneous electrical nerve stimulation (TENS) in angina pectoris", *Pain*, 26(3), (Sep. 1986),291-300.

Mannheimer, C, et al., "Transcutaneous electrical nerve stimulation in severe angina pectoris", *European Heart Journal*, 3(4), (Aug. 1982),297-302.

Mazgalev, T N., et al., "Autonomic modification of the atrioventricular node during atrial fibrillation: role in the slowing of ventricular rate", *Circulation*, 99(21), (Jun. 1, 1999),2806-14.

Millar-Craig, M W., et al., "Circadian variation of blood-pressure", *Lancet*, 1(8068), (Apr. 15, 1978),795-7.

Minisi, A J., et al., "Regional left ventricular deafferentation increases baroreflex sensitivity following myocardial infarction", *Cardiovasc Res.*, 58(1), (Apr. 1, 2003),136-41.

Murphy, D F., et al., "Intractable angina pectoris: management with dorsal column stimulation", *Medical Journal of Australia*, 146(5), (Mar. 2, 1987),260.

Neistadt, A, et al., "Effects of electrical stimulation of the carotid sinus nerve in reversal of experimentally induced hypertension", *Surgery*, 61(6), (Jun. 1967),923-31.

Pastore, Joseph M., et al., "Multi-Site Ventricular Pacing Therapy With Parasympathetic Stimulation", U.S. Appl. No. 10/700,368, filed Nov. 3, 2003, 18 pgs.

Peter, T K., et al., "Temporal and spatial summation caused by aortic nerve stimulation in rabbits. Effects of stimulation frequencies and amplitudes", *Journal of the Autonomic Nervous System*, 27(3), (Aug. 1989),193-205.

Peters, T K., et al., "The principle of electrical carotid sinus nerve stimulation: a nerve pacemaker system for angina pectoris and hypertension therapy", *Annals of Biomedical Engineering*, 8(4-6), (1980),445-58.

Philbin, D M., et al., "Inappropriate shocks delivered by an ICD as a result of sensed potentials from a transcutaneous electronic nerve stimulation unit", *Pacing & Clinical Electrophysiology*, 21(10), (Oct. 1998),2010-1.

Prakash, P, et al., "Asymmetrical distribution of aortic nerve fibers in the pig", *Anat Rec.*, 158(1), (May 1967),51-7.

Rosenqvist, M, "The effect of ventricular activation sequence on cardiac performance during pacing", *Pacing and Electrophysiology*, 19(9), (1996),1279-1286.

Rushmer, Robert F., "Chapter 5—Systemic Arterial Pressure", *In: Cardiovascular dynamics*, Philadelphia : Saunders,(1976),176-216.

Schauerte, P, et al., "Catheter stimulation of cardiac parasympathetic nerves in humans: a novel approach to the cardiac autonomic nervous system", *Circulation*, 104(20), (Nov. 13, 2001),2430-5.

Schauerte, P N., et al., "Transvenous parasympathetic cardiac nerve stimulation: an approach for stable sinus rate control", *Journal of Cardiovascular Electrophysiology*, 10(11), (Nov. 1999),1517-24.

Schauerte, P, "Transvenous Parasympathetic Nerve Stimulation in the Inferior Vena Cava and Atrioventricular Conduction", *Journal of Cardiovascular Electrophysiology*, 11(1), (Jan. 2000),64-69.

Schauerte, P, et al., "Ventricular rate control during atrial fibrillation by cardiac parasympathetic nerve stimulation: a transvenous approach", *Journal of the American College of Cardiology*, 34(7), (Dec. 1999),2043-50.

Scheiner, Avram, et al., "Stimulation Lead for Stimulating the Baroreceptors in the Pulmonary Artery", U.S. Appl. No. 10/745,852, filed Dec. 24, 2003, 25 pgs.

Scherlag, M A., "Endovascular Neural Stimulation Via a Novel Basket Electrode Catheter: Comparison of Electrode Configurations", *Journal of Interventional Cardiac Electrophysiology*, 4(1), (Apr. 2000),219-224.

Takahashi, N, "Vagal modulation of ventricular tachyarrhythmias induced by left ansae subclaviae stimulation in rabbits", *Japanese Heart Journal*, 39(4), (Jul. 1998),503-11.

Tse, H F., et al., "Long-term effect of right ventricular pacing on myocardial perfusion and function", *J Am Coll Cardiol.*, 29(4), (Mar. 15, 1997),744-9.

Vanoli, E, "Vagal stimulation and prevention of sudden death in conscious dogs with a healed myocardial infarction", *Circulation Research*, 68(5), (May 1991),1471-81.

Veerman, D P., et al., "Circadian profile of systemic hemodynamics", *Hypertension*, 26(1), (Jul. 1995),55-9.

Verity, M A., et al., "Plurivesicular nerve endings in the pulmonary artery", *Nature*, 211(48), (Jul. 30, 1966),537-8.

Verity, M, et al., "Pulmonary artery innervation: a morphopharmacologic correlation", *Proceedings of the Western Pharmacology Society*, 8, (1965),57-9.

Wallick, D W., "Selective AV nodal vagal stimulation improves hemodynamics during acute atrial fibrillation in dogs", *American Journal of Physiology—Heart & Circulatory Physiology*, 281(4), (Oct. 2001),H1490-7.

Waninger, M S., et al., "Electrophysiological control of ventricular rate during atrial fibrillation", *Pacing & Clinical Electrophysiology*, 23(8), (Aug. 2000),1239-44.

Wiggers, C J., et al., "The muscular reactions of the mammalian ventricles to artificial surface stimuli", *American Journal of Physiology*, (1925),346-378.

Zhang, Y, et al., "Optimal ventricular rate slowing during atrial fibrillation by feedback AV nodal-selective vagal stimulation", *American Journal of Physiology—Heart & Circulatory Physiology*, 282(3), (Mar. 2002),H1102-10.

Zhou, X, et al., "Prevention of high incidence of neurally mediated ventricular arrhythmias by afferent nerve stimulation in dogs", *Circulation*, 101(7), (Feb. 22, 2000),819-24.

Libbus, Imad, "Barofeflex Therapy for Disordered Breathing", U.S. Appl. No. 10/864,070, filed Jun. 8, 2004, 71 pgs.

Libbus, Imad, "Baroreflex Modulation Based on Monitored Cardiovascular Parameter", U.S. Appl. No. 10/939,544, filed Sep. 13, 2004, 75 pgs.

Chapleau, Mark W., "Contrasting effects of static and pulsatile pressure on carotid baroreceptor activity in dogs", *Circulation*, vol. 61, No. 5, (Nov. 1987), 648-658.

Chapleau, Mark W., "Pulsatile activation of baroreceptors causes central facilitation of baroreflex", *American Journal Physiol Heart Circ Physiol*, (Jun. 1989), 256: H1735-1741.

Chavan, Abhi, et al., "Implantable and Rechargeable Neural Stimulator", U.S. Appl. No. 11/256,907, filed Oct. 24, 2005, 35 Pages.

Janes, R. D., "Anatomy of human extrinsic cardiac nerves and ganglia.", *Am J Cardiol.*, 57(4), (Feb. 1, 1986), 299-309.

Li, Meihua, "Vagal nerve stimulation markedly improves long-term survival after chronic heart failure in rats", *Circulation*, 109(1), Epub Dec. 8, 2003,(Jan. 6, 2004), 1-5.

Libbus, Imad, "Implantable Device for Treating Epilepsy and Cardiac Rhythm Disorders", U.S. Appl. No. 11/312,178, filed Dec. 21, 2005, 39 Pages.

Libbus, I., "Integrated Lead for Applying Cardiac Resynchronization Therapy and Neural Stimulation Therapy", U.S. Appl. No. 11/077,970, filed Mar. 11, 2005, 67 pgs.

Libbus, I., et al., "Method and Apparatus for Synchronizing Neural Simulation to Cardiac Cycles", U.S. Appl. No. 11/099,141, filed Apr. 5, 2005.

Libbus, Imad, "System to Provide Myocardial and Neural Stimulation", U.S. Appl. No. 11/087,935, filed Mar. 23, 2005, 52 pgs.

Moffitt, Julia, "Combined Neural Stimulation and Cardiac Resynchronization Therapy", U.S. Appl. No. 11/078,460, filed Mar. 11, 2005, 35 pgs.

Huikuri, H., et al., "Circadian rhythms of frequency domain measures of heart rate variability in healthy subjects and patients with coronary artery disease. Effects of arousal and upright posture.", *Circulation*, 90(1), (1994),121-126.

Libbus, Imad, "Automatic Neural Stimulation Modulation Based on Activity", U.S. Appl. No. 11/558,083, filed Nov. 9, 2006, 76 Pages.

Muller, J., "Circadian variation and triggers of onset of acute cardiovascular disease", *Circulation*, 79(4), (1989),733-743.

"Devices and Methods for Cardiovascular Reflex Control", U.S. Appl. No. 60/368,222, filed Mar. 27, 2002, 146 Pages.

"Preliminary Statement U.S. Appl. No. 11/482,453 dated Oct. 31, 2006", 3 Pages.

Kieval, Robert, et al., "Devices and Methods for Cardiovascular Reflex Control", U.S. Appl. No. 10/284,063, filed Oct. 29, 2002, 52 Pages.

Non-Final Office Action mailed by the USPTO on Apr. 26, 2007 for related matter U.S. Appl. No. 10/746,846, 18 Pages.

Non-Final Office Action mailed Jul. 12, 2007 in U.S. Appl. No. 10/746,861, OARN, 21 pages.

Non-Final Office Action mailed Jul. 19, 2007 in U.S. Appl. No. 10/746,135, OARN, 27 pages.

Preliminary Statement U.S. Appl. No. 11/482,225 dated Oct. 31, 2006, 2 pages.

Preliminary Statement U.S. Appl. No. 11/482,264, Dated Oct. 30, 2006, 1 page.

Preliminary Statement U.S. Appl. No. 11/482,635, Dated Oct. 31, 2006, 2 pages.

Preliminary Statement U.S. Appl. No. 11/482,662 dated Oct. 31, 2006, 2 pages.

Substitute Preliminary Statement U.S. Appl. No. 11/428,131 dated Jul. 5, 2006, 2 pages.

Coleridge, J. C., et al., "Reflex effects of stimulating baroreceptors in the pulmonary artery", *J. Physiol*, 166, (1963),197-210.

Libbus, Imad, et al., "Sensing With Compensation for Neural Stimulator", U.S. Appl. No. 11/621,194, filed Jan. 9, 2007, 69 pgs.

"Preliminary Statement U.S. Appl. No. 11/482,505, Dated Oct. 31, 2006", 2 Pages.

"Preliminary Statement U.S. Appl. No. 11/482,563, Dated Oct. 31, 2006", 2 Pages.

\* cited by examiner

BAROREFLEX STIMULATION SYNCHRONIZED TO CIRCADIAN RHYTHM

CROSS REFERENCE TO RELATED APPLICATIONS

The following commonly assigned U.S. patent applications are related, are all filed on the same date as the present application and are all herein incorporated by reference in their entirety: "Baroreflex Stimulation System to Reduce Hypertension," U.S. patent application Ser. No. 10/746,134, filed on Dec. 24, 2003; "Sensing With Compensation for Neural Stimulator," U.S. patent application Ser. No. 10/746,847, filed on Dec. 24, 2003; "Implantable Baroreflex Stimulator with Integrated Pressure Sensor," U.S. patent application Ser. No. 10/745,921, filed on Dec. 24, 2003; "Automatic Baroreflex Modulation Based on Cardiac Activity," U.S. patent application Ser. No. 10/746,846, filed on Dec. 24, 2003; "Automatic Baroreflex Modulation Responsive to Adverse Event," U.S. patent application Ser. No. 10/745,925, filed on Dec. 24, 2003; "Baroreflex Modulation to Gradually Increase Blood Pressure," U.S. patent application Ser. No. 10/746,845,filed on Dec. 24, 2003; "Baroreflex Stimulation to Treat Acute Myocardial Infarction," U.S. patent application Ser. No. 10/745,920, filed on Dec. 24, 2003; "Baropacing and Cardiac Pacing to Control Output," U.S. patent application Ser. No. 10/746,135, filed on Dec. 24, 2003; "Baroreflex Stimulation Synchronized to Circadian Rhythm," U.S. patent application Ser. No. 10/746,844, filed on Dec. 24, 2003; "A Lead for Stimulating the Baroreflex in the Pulmonary Artery," U.S. patent application Ser. No. 10/746,861, filed on Dec. 24,2003; and "A Stimulation Lead for Stimulating the Baroreceptors in the Pulmonary Artery," U.S. patent application Ser. No. 10/746,852, filed on Dec. 24,2003.

TECHNICAL FIELD

This application relates generally to implantable medical devices and, more particularly, to synchronizing baroreflex stimulation to circadian rhythm.

BACKGROUND

Implanting a chronic electrical stimulator, such as a cardiac stimulator, to deliver medical therapy(ies) is known. Examples of cardiac stimulators include implantable cardiac rhythm management (CRM) device such as pacemakers, implantable cardiac defibrillators (ICDs), and implantable devices capable of performing pacing and defibrillating functions.

CRM devices are implantable devices that provide electrical stimulation to selected chambers of the heart in order to treat disorders of cardiac rhythm. An implantable pacemaker, for example, is a CRM device that paces the heart with timed pacing pulses. If functioning properly, the pacemaker makes up for the heart's inability to pace itself at an appropriate rhythm in order to meet metabolic demand by enforcing a minimum heart rate. Some CRM devices synchronize pacing pulses delivered to different areas of the heart in order to coordinate the contractions. Coordinated contractions allow the heart to pump efficiently while providing sufficient cardiac output.

Heart failure refers to a clinical syndrome in which cardiac function causes a below normal cardiac output that can fall below a level adequate to meet the metabolic demand of peripheral tissues. Heart failure may present itself as congestive heart failure (CHF) due to the accompanying venous and pulmonary congestion. Heart failure can be due to a variety of etiologies such as ischemic heart disease.

Hypertension is a cause of heart disease and other related cardiac co-morbidities. Hypertension occurs when blood vessels constrict. As a result, the heart works harder to maintain flow at a higher blood pressure, which can contribute to heart failure. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

A pressoreceptive region or field is capable of sensing changes in pressure, such as changes in blood pressure. Pressoreceptor regions are referred to herein as baroreceptors, which generally include any sensors of pressure changes. For example, baroreceptors include afferent nerves and further include sensory nerve endings that are sensitive to the stretching of the wall that results from increased blood pressure from within, and function as the receptor of a central reflex mechanism that tends to reduce the pressure. Baroreflex functions as a negative feedback system, and relates to a reflex mechanism triggered by stimulation of a baroreceptor. Increased pressure stretches blood vessels, which in turn activates baroreceptors in the vessel walls. Activation of baroreceptors naturally occurs through internal pressure and stretching of the arterial wall, causing baroreflex inhibition of sympathetic nerve activity (SNA) and a reduction in systemic arterial pressure. An increase in baroreceptor activity induces a reduction of SNA, which reduces blood pressure by decreasing peripheral vascular resistance.

The general concept of stimulating afferent nerve trunks leading from baroreceptors is known. For example, direct electrical stimulation has been applied to the vagal nerve and carotid sinus. Research has indicated that electrical stimulation of the carotid sinus nerve can result in reduction of experimental hypertension, and that direct electrical stimulation to the pressoreceptive regions of the carotid sinus itself brings about reflex reduction in experimental hypertension.

Electrical systems have been proposed to treat hypertension in patients who do not otherwise respond to therapy involving lifestyle changes and hypertension drugs, and possibly to reduce drug dependency for other patients.

SUMMARY

Various aspects and embodiments of the present subject matter provide baroreflex stimulation that mimics the natural circadian rhythm by providing stimulation levels that rise and fall during the day. Such stimulation, for example, promotes sleep or rest during certain portions of the day and promotes activity during other portions of the day.

An aspect of the present subject matter relates to a baroreflex stimulator. An embodiment of the stimulator comprises a pulse generator to provide a baroreflex stimulation signal through an electrode, and a modulator to modulate the baroreflex stimulation signal based on a circadian rhythm template.

An aspect of the present subject matter relates to a baroreflex stimulator. An embodiment of the stimulator comprises a pulse generator to provide a baroreflex stimulation signal through an electrode, and means for modulating the baroreflex stimulation signal based on a circadian rhythm.

An aspect of the present subject matter relates to a method for operating an implantable medical device. In an embodiment, a baroreflex stimulation therapy is applied using a baroreflex stimulator in the implantable medical device. The baroreflex stimulation therapy is modulated based on a circadian rhythm template. In one method embodiment, a circadian rhythm template is accessed, a baroreflex stimulation level is set based on the circadian rhythm template. Baroreflex stimulation is applied at the baroreflex stimulation level to a baroreceptor site in a pulmonary artery.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1B:
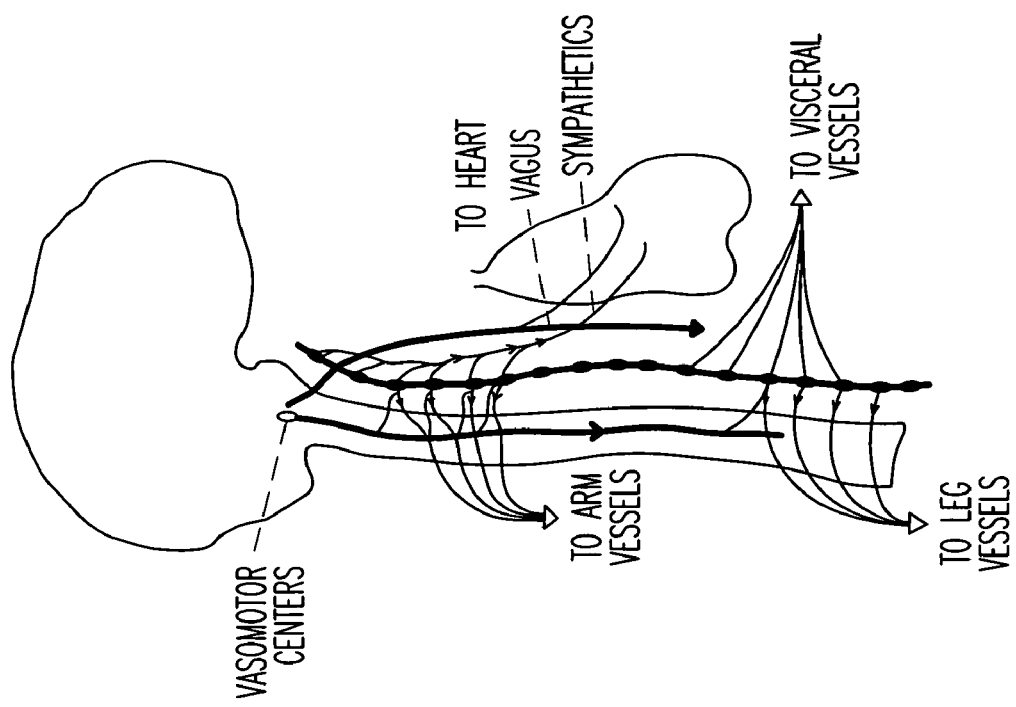
FIGS. 1A and 1B illustrate neural mechanisms for peripheral vascular control.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Hypertension and Baroreflex Physiology

A brief discussion of hypertension and the physiology related to baroreceptors is provided to assist the reader with understanding this disclosure. This brief discussion introduces hypertension, the autonomic nervous system, and baroreflex.

Hypertension is a cause of heart disease and other related cardiac co-morbidities. Hypertension generally relates to high blood pressure, such as a transitory or sustained elevation of systemic arterial blood pressure to a level that is likely to induce cardiovascular damage or other adverse consequences. Hypertension has been arbitrarily defined as a systolic blood pressure above 140 mm Hg or a diastolic blood pressure above 90 mm Hg. Hypertension occurs when blood vessels constrict. As a result, the heart works harder to maintain flow at a higher blood pressure. Consequences of uncontrolled hypertension include, but are not limited to, retinal vascular disease and stroke, left ventricular hypertrophy and failure, myocardial infarction, dissecting aneurysm, and renovascular disease.

The automatic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes, but is not limited to, the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

Figure 1A:
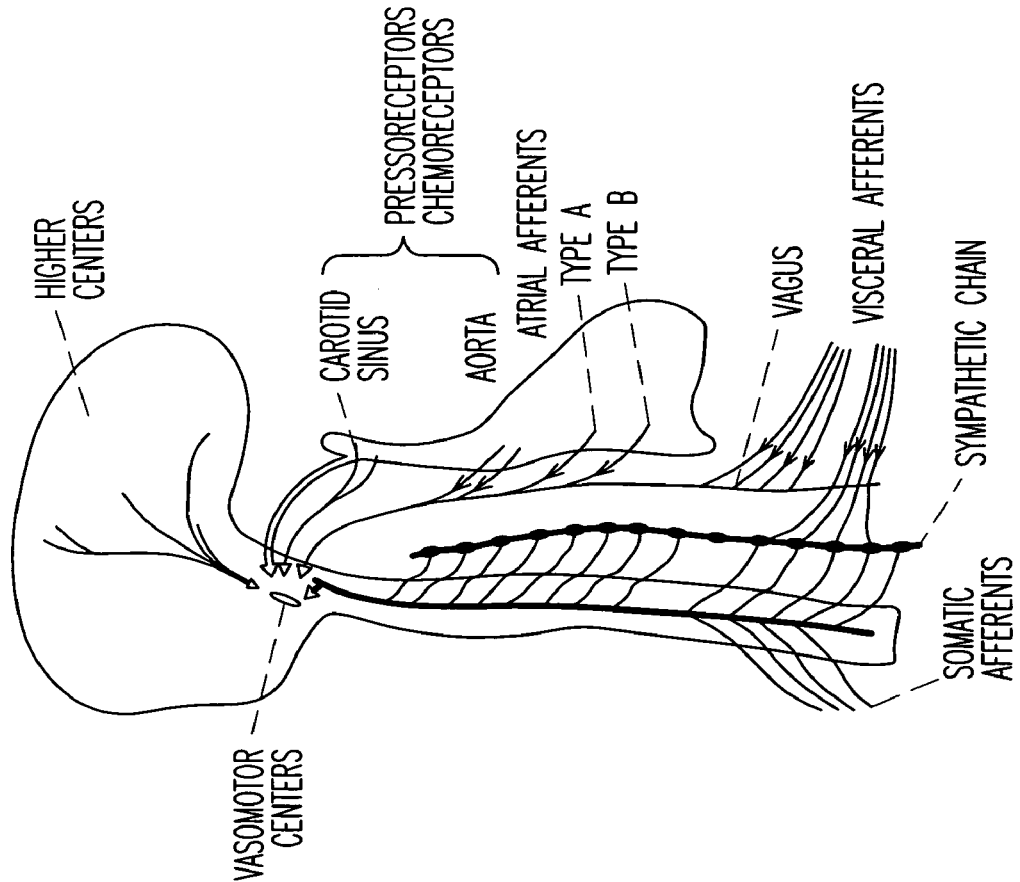

The subject matter of this disclosure generally refers to the effects that the ANS has on the heart rate and blood pressure, including vasodilation and vasoconstriction. The heart rate and force is increased when the sympathetic nervous system is stimulated, and is decreased when the sympathetic nervous system is inhibited (the parasympathetic nervous system is stimulated). FIGS. 1A and 1B illustrate neural mechanisms for peripheral vascular control. FIG. 1A generally illustrates afferent nerves to vasomotor centers. An afferent nerve conveys impulses toward a nerve center. A vasomotor center relates to nerves that dilate and constrict blood vessels to control the size of the blood vessels. FIG. 1B generally illustrates efferent nerves from vasomotor centers. An efferent nerve conveys impulses away from a nerve center.

Stimulating the sympathetic and parasympathetic nervous systems can have effects other than heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other. Thus, an indiscriminate stimulation of the sympathetic and/or parasympathetic nervous systems to achieve a desired response, such as vasodilation, in one physiological system may also result in an undesired response in other physiological systems.

Baroreflex is a reflex triggered by stimulation of a baroreceptor. A baroreceptor includes any sensor of pressure changes, such as sensory nerve endings in the wall of the auricles of the heart, cardiac fat pads, vena cava, aortic arch and carotid sinus, that is sensitive to stretching of the wall resulting from increased pressure from within, and that functions as the receptor of the central reflex mechanism that tends to reduce that pressure. Additionally, a baroreceptor includes afferent nerve trunks, such as the vagus, aortic and carotid nerves, leading from the sensory nerve endings. Stimulating baroreceptors inhibits sympathetic nerve activity (stimulates the parasympathetic nervous system) and reduces systemic arterial pressure by decreasing peripheral vascular resistance and cardiac contractility. Baroreceptors are naturally stimulated by internal pressure and the stretching of the arterial wall.

Some aspects of the present subject matter locally stimulate specific nerve endings in arterial walls rather than stimulate afferent nerve trunks in an effort to stimulate a desire response (e.g. reduced hypertension) while reducing the undesired effects of indiscriminate stimulation of the nervous system. For example, some embodiments stimulate baroreceptor sites in the pulmonary artery. Some embodiments of the present subject matter involve stimulating either baroreceptor sites or nerve endings in the aorta, the chambers of the heart, and the fat pads of the heart, and some embodiments of the present subject matter involve stimulating an afferent nerve trunk, such as the vagus, carotid and aortic nerves. Some embodiments stimulate afferent nerve trunks using a cuff electrode, and some embodiments stimulate afferent nerve trunks using an intravascular lead positioned lead positioned in a blood vessel proximate to the nerve, such that the electrical stimulation passes through the vessel wall to stimulate the afferent nerve trunk.

Figure 2B:
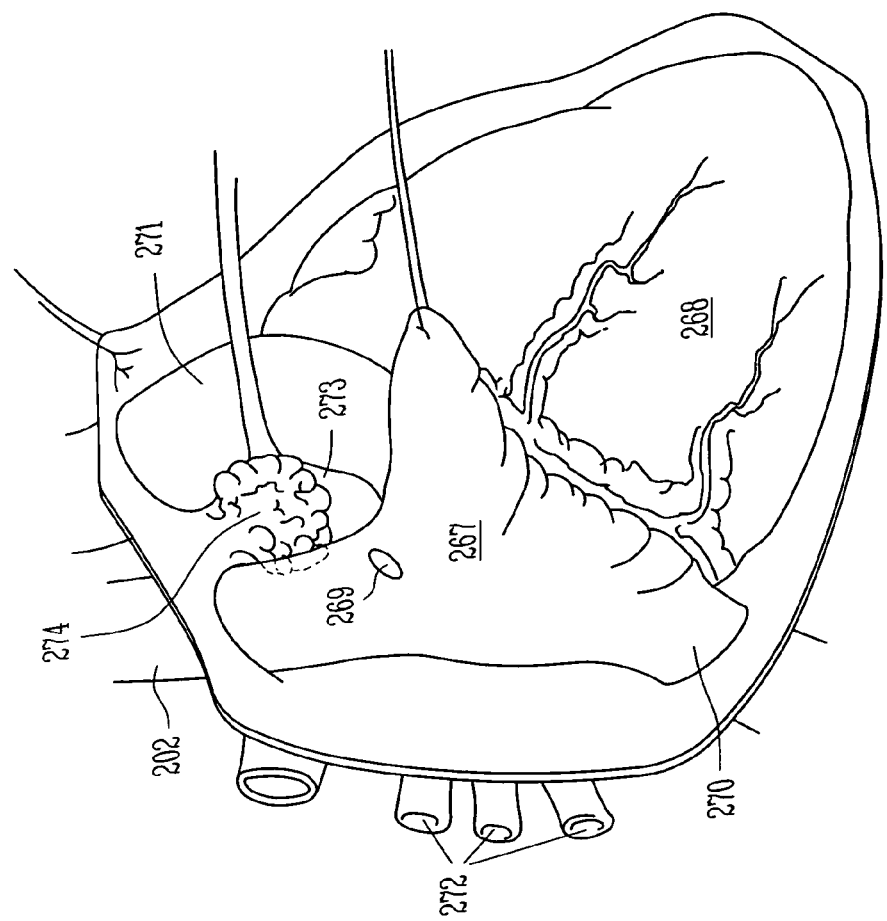
FIGS. 2A-2C illustrate a heart.
Figure 2A:
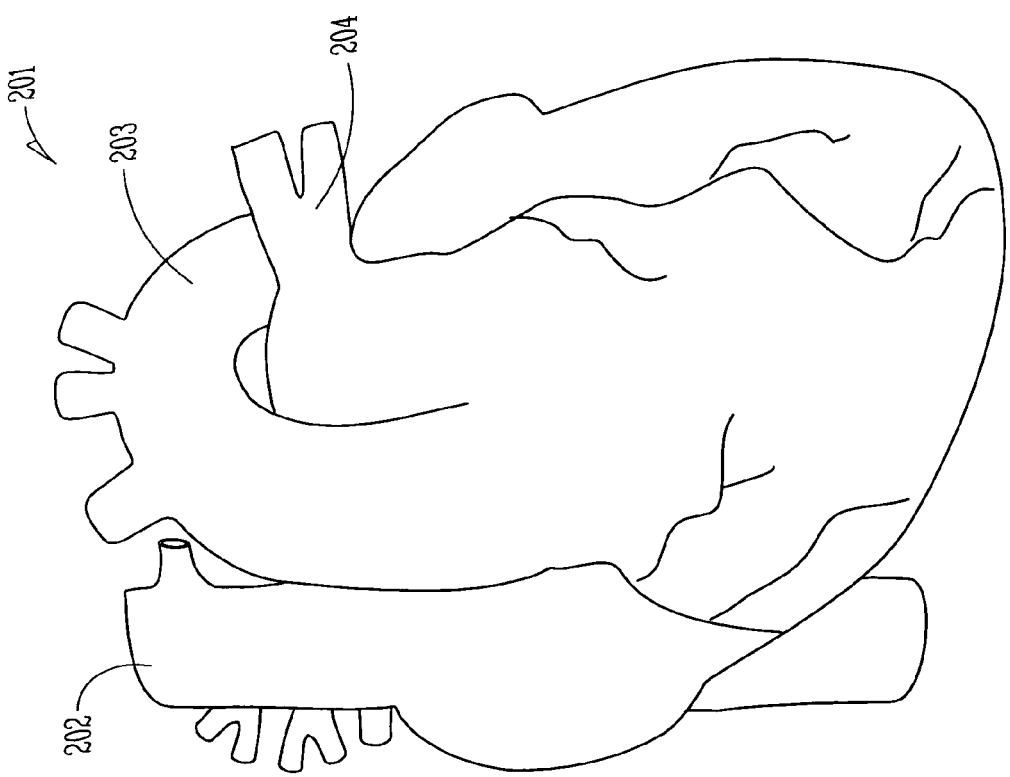
Figure 2C:
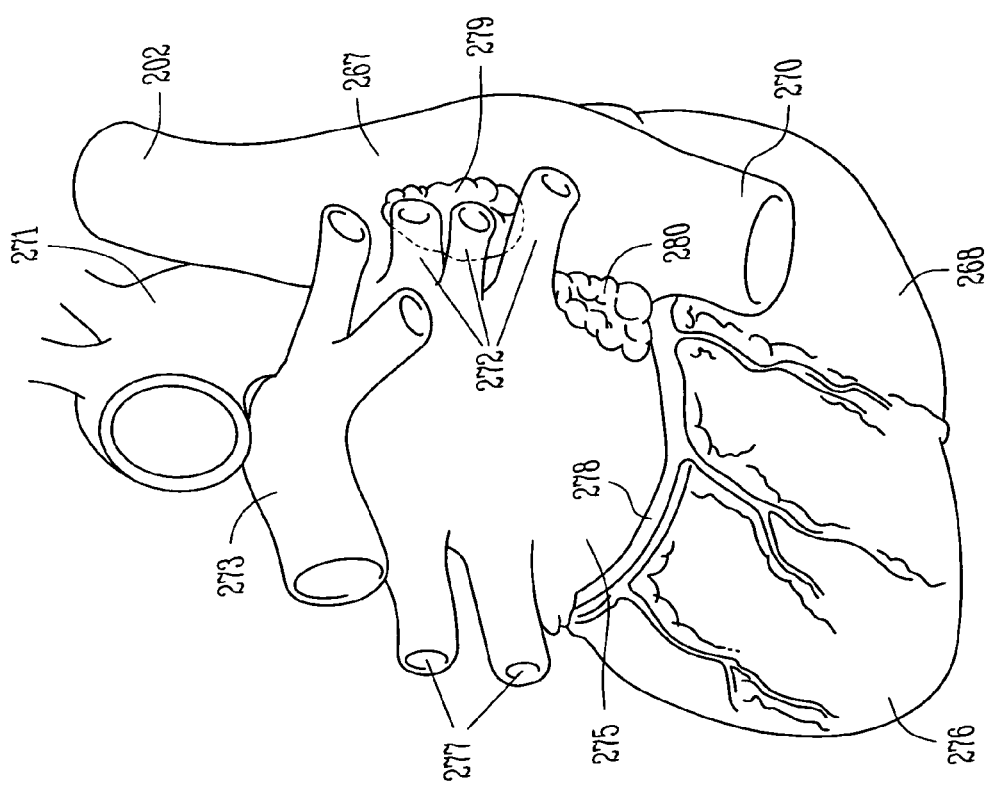

FIGS. 2A-2C illustrate a heart. As illustrated in FIG. 2A, the heart 201 includes a superior vena cava 202, an aortic arch 203, and a pulmonary artery 204, and is useful to provide a contextual relationship with the illustrations in FIGS. 3-5. As is discussed in more detail below, the pulmonary artery 204 includes baroreceptors. A lead is capable of being intravascularly inserted through a peripheral vein and through the tricuspid valve into the right ventricle of the heart (not expressly shown in the figure) similar to a cardiac pacemaker lead, and continue from the right ventricle through the pulmonary valve into the pulmonary artery. A portion of the pulmonary artery and aorta are proximate to each other. Various embodiments stimulate baroreceptors in the aorta using a lead intravascularly positioned in the pulmonary artery. Thus, according to various aspects of the present subject matter, the baroreflex is stimulated in or around the pulmonary artery by at least one electrode intravascularly inserted into the pulmonary artery. Alternatively, a wireless stimulating device, with or without pressure sensing capability, may be positioned via catheter into the pulmonary artery. Control of stimulation and/or energy for stimulation may be supplied by another implantable or external device via ultrasonic, electromagnetic or a combination thereof. Aspects of the present subject matter provide a relatively noninvasive surgical technique to implant a baroreceptor stimulator intravascularly into the pulmonary artery.

FIGS. 2B-2C illustrate the right side and left side of the heart, respectively, and further illustrate cardiac fat pads which have nerve endings that function as baroreceptor sites. FIG. 2B illustrates the right atrium 267, right ventricle 268, sinoatrial node 269, superior vena cava 202, inferior vena cava 270, aorta 271, right pulmonary veins 272, and right pulmonary artery 273. FIG. 2B also illustrates a cardiac fat pad 274 between the superior vena cava and aorta. Baroreceptor nerve endings in the cardiac fat pad 274 are stimulated in some embodiments using an electrode screwed into the fat pad, and are stimulated in some embodiments using an intravenously-fed lead proximately positioned to the fat pad in a vessel such as the right pulmonary artery or superior vena cava, for example. FIG. 2C illustrates the left atrium 275, left ventricle 276, right atrium 267, right ventricle 268, superior vena cava 202, inferior vena cava 270, aorta 271, right pulmonary veins 272, left pulmonary vein 277, right pulmonary artery 273, and coronary sinus 278. FIG. 2C also illustrates a cardiac fat pad 279 located proximate to the right cardiac veins and a cardiac fat pad 280 located proximate to the inferior vena cava and left atrium. Baroreceptor nerve endings in the fat pad 279 are stimulated in some embodiments using an electrode screwed into the fat pad 279, and are stimulated in some embodiments using an intravenously-fed lead proximately positioned to the fat pad in a vessel such as the right pulmonary artery 273 or right pulmonary vein 272, for example. Baroreceptors in the 280 are stimulated in some embodiments using an electrode screwed into the fat pad, and are stimulated in some embodiments using an intravenously-fed lead proximately positioned to the fat pad in a vessel such as the inferior vena cava 270 or coronary sinus or a lead in the left atrium 275, for example.

Figure 3:
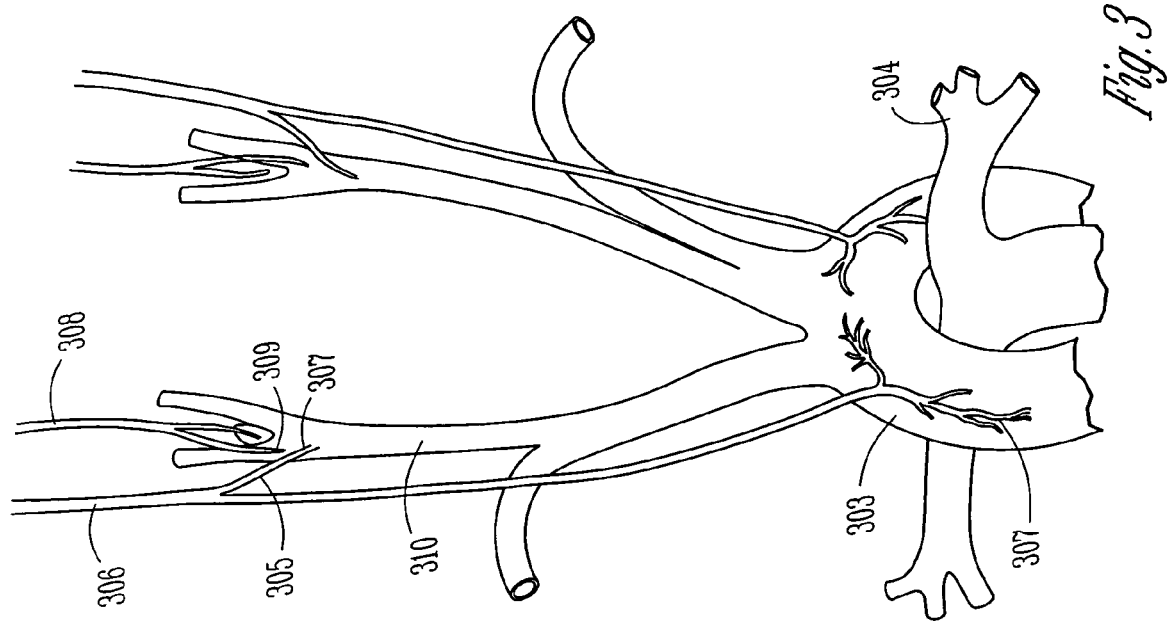
FIG. 3 illustrates baroreceptors and afferent nerves in the area of the carotid sinuses and aortic arch.

FIG. 3 illustrates baroreceptors in the area of the carotid sinuses 305, aortic arch 303 and pulmonary artery 304. The aortic arch 303 and pulmonary artery 304 were previously illustrated with respect to the heart in FIG. 2A. As illustrated in FIG. 3, the vagus nerve 306 extends and provides sensory nerve endings 307 that function as baroreceptors in the aortic arch 303, in the carotid sinus 305 and in the common carotid artery 310. The glossopharyngeal nerve 308 provides nerve endings 309 that function as baroreceptors in the carotid sinus 305. These nerve endings 307 and 309, for example, are sensitive to stretching of the wall resulting from increased pressure from within. Activation of these nerve endings reduce pressure. Although not illustrated in the figures, the fat pads and the atrial and ventricular chambers of the heart also include baroreceptors. Cuffs have been placed around afferent nerve trunks, such as the vagal nerve, leading from baroreceptors to vasomotor centers to stimulate the baroreflex. According to various embodiments of the present subject matter, afferent nerve trunks can be stimulated using a cuff or intravascularly-fed lead positioned in a blood vessel proximate to the afferent nerves.

Figure 5:
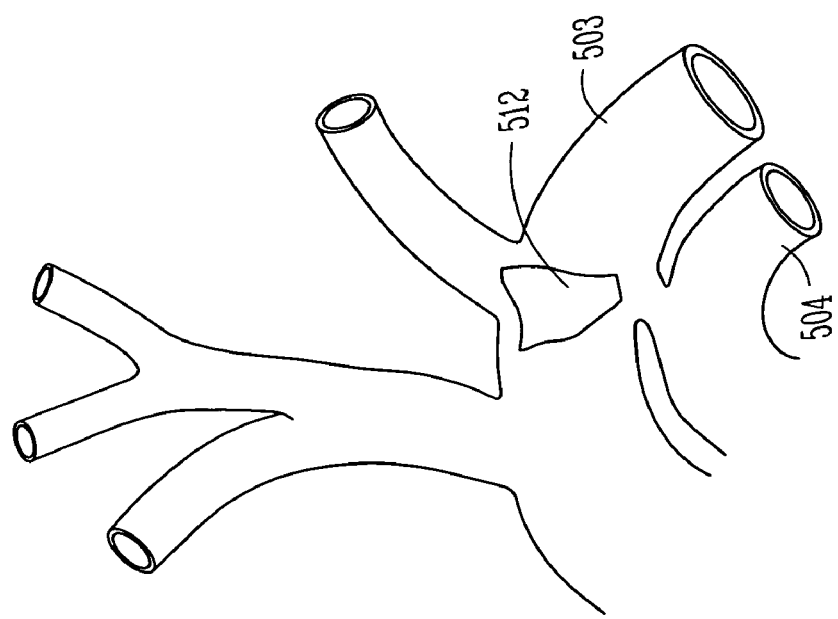
FIG. 5 illustrates baroreceptor fields in the aortic arch, the ligamentum arteriosum and the trunk of the pulmonary artery.
Figure 4:
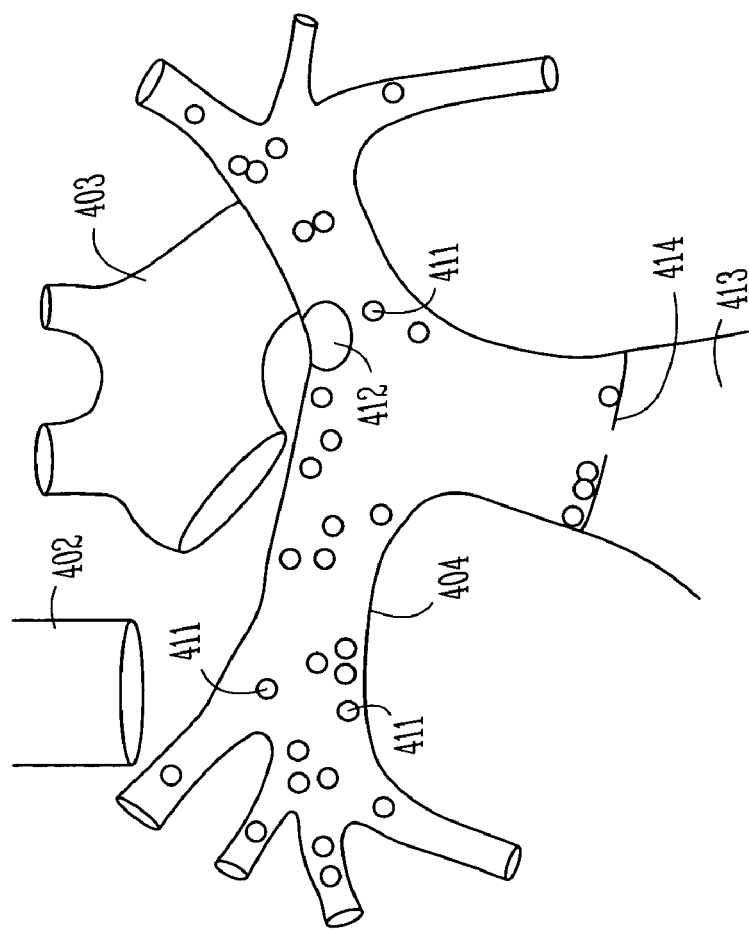
FIG. 4 illustrates baroreceptors in and around the pulmonary artery.

FIG. 4 illustrates baroreceptors in and around a pulmonary artery 404. The superior vena cava 402 and the aortic arch 403 are also illustrated. As illustrated, the pulmonary artery 404 includes a number of baroreceptors 411, as generally indicated by the dark area. Furthermore, a cluster of closely spaced baroreceptors is situated near the attachment of the ligamentum arteriosum 412. FIG. 4 also illustrates the right ventricle 413 of the heart, and the pulmonary valve 414 separating the right ventricle 413 from the pulmonary artery 404. According to various embodiments of the present subject matter, a lead is inserted through a peripheral vein and threaded through the tricuspid valve into the right ventricle, and from the right ventricle 413 through the pulmonary valve 414 and into the pulmonary artery 404 to stimulate baroreceptors in and/or around the pulmonary artery. In various embodiments, for example, the lead is positioned to stimulate the cluster of baroreceptors near the ligamentum arteriosum 412. FIG. 5 illustrates baroreceptor fields 512 in the aortic arch 503, near the ligamentum arteriosum and the trunk of the pulmonary artery 504. Some embodiments position the lead in the pulmonary artery to stimulate baroreceptor sites in the aorta and/or fat pads, such as are illustrated in FIGS. 2B-2C.

Figure 6:
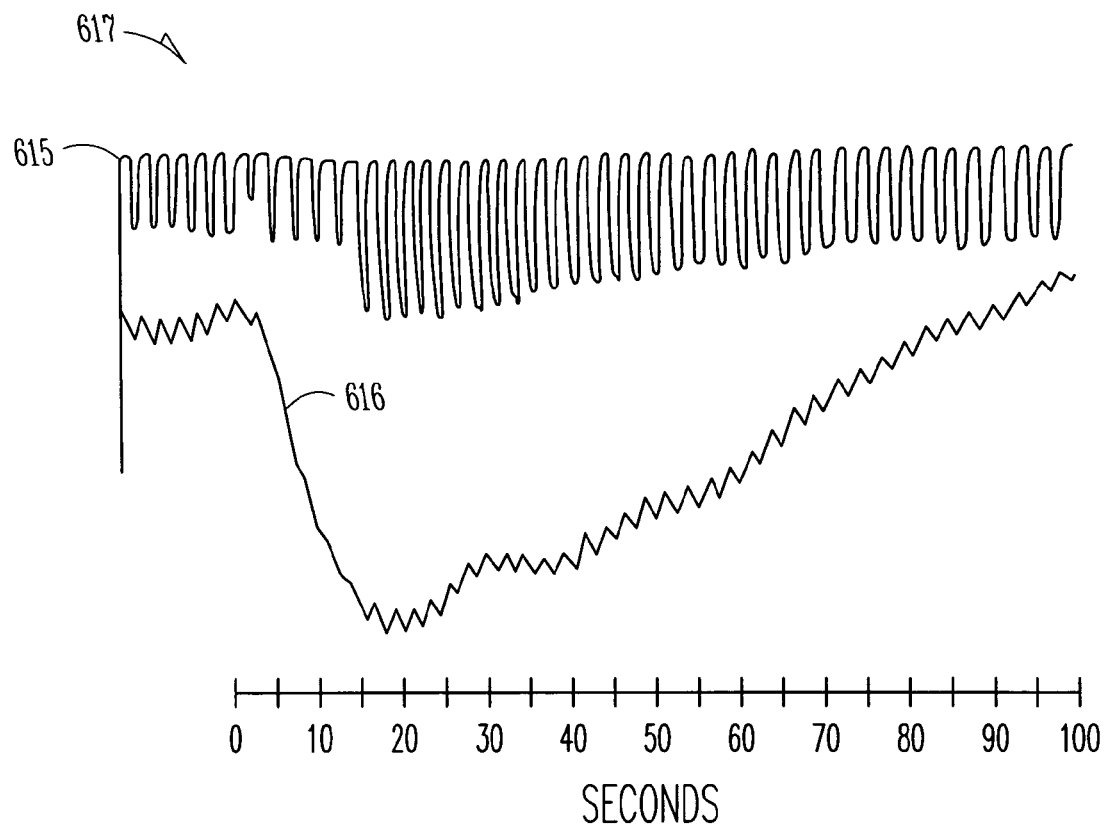
FIG. 6 illustrates a known relationship between respiration and blood pressure when the baroreflex is stimulated.

FIG. 6 illustrates a known relationship between respiration 615 and blood pressure 616 when the left aortic nerve is stimulated. When the nerve is stimulated at 617, the blood pressure 616 drops, and the respiration 615 becomes faster and deeper, as illustrated by the higher frequency and amplitude of the respiration waveform. The respiration and blood pressure appear to return to the pre-stimulated state in approximately one to two minutes after the stimulation is removed. Various embodiments of the present subject matter use this relationship between respiration and blood pressure by using respiration as a surrogate parameter for blood pressure.

Figure 7:
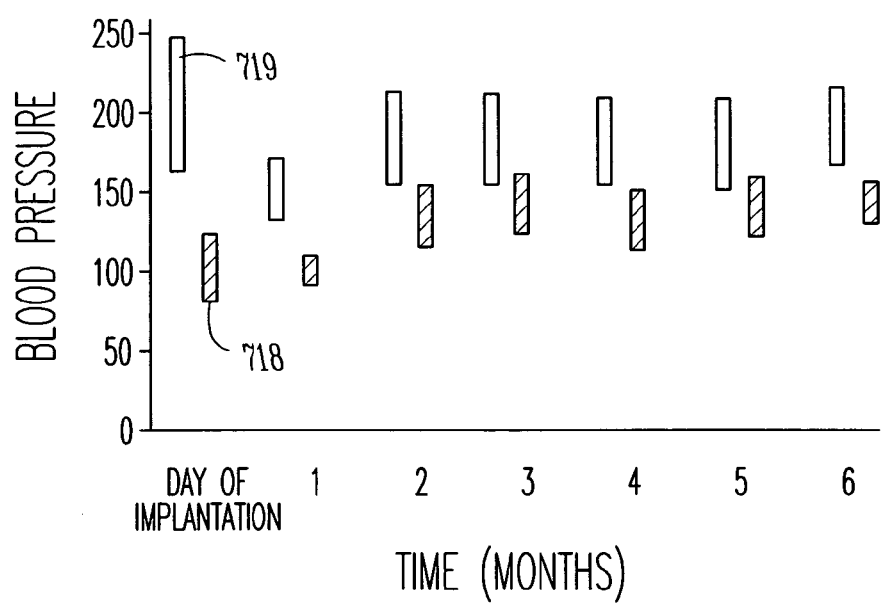
FIG. 7 illustrates a blood pressure response to carotid nerve stimulation in a hypertensive dog during 6 months of intermittent carotid nerve stimulation.

FIG. 7 illustrates a known blood pressure response to carotid nerve stimulation in a hypertensive dog during 6 months of intermittent carotid nerve stimulation. The figure illustrates that the blood pressure of a stimulated dog 718 is significantly less than the blood pressure of a control dog 719 that also has high blood pressure. Thus, intermittent stimulation is capable of triggering the baroreflex to reduce high blood pressure.

Baroreflex Stimulator Systems

Various embodiments of the present subject matter relate to baroreflex stimulator systems. Such baroreflex stimulation systems are also referred to herein as neural stimulator (NS) devices or components. Examples of neural stimulators include anti-hypertension (AHT) devices or AHT components that are used to treat hypertension. Various embodiments of the present subject matter include stand-alone implantable baroreceptor stimulator systems, include implantable devices that have integrated NS and cardiac rhythm management (CRM) components, and include systems with at least one implantable NS device and an implantable CRM device capable of communicating with each other either wirelessly or through a wire lead connecting the implantable devices. Integrating NS and CRM functions that are either performed in the same or separate devices improves aspects of the NS therapy and cardiac therapy by allowing these therapies to work together intelligently.

Figure 8:
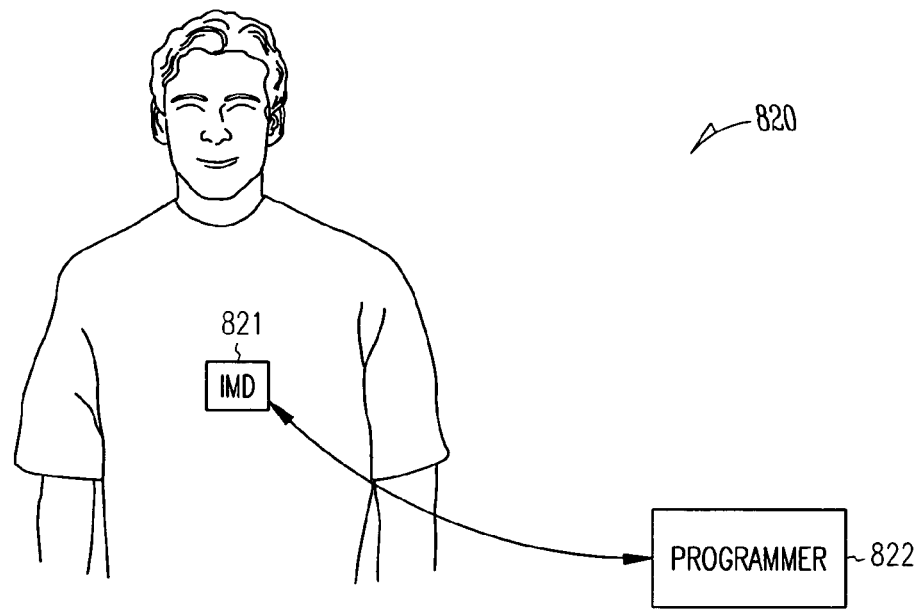
FIG. 8 illustrates a system including an implantable medical device (IMD) and a programmer, according to various embodiments of the present subject matter.

FIG. 8 illustrates a system 820 including an implantable medical device (IMD) 821 and a programmer 822, according to various embodiments of the present subject matter. Various embodiments of the IMD 821 include neural stimulator functions only, and various embodiments include a combination of NS and CRM functions. Some embodiments of the neural stimulator provide ART functions. The programmer 822 and the IMD 821 are capable of wirelessly communicating data and instructions. In various embodiments, for example, the programmer 822 and IMD 821 use telemetry coils to wirelessly communicate data and instructions. Thus, the programmer can be used to adjust the programmed therapy provided by the IMD 821, and the IMD can report device data (such as battery and lead resistance) and therapy data (such as sense and stimulation data) to the programmer using radio telemetry, for example. According to various embodiments, the IMD 821 stimulates baroreceptors to provide NS therapy such as AHT therapy. Various embodiments of the IMD 821 stimulate baroreceptors in the pulmonary artery using a lead fed through the right ventricle similar to a cardiac pacemaker lead, and further fed into the pulmonary artery. According to various embodiments, the IMD 821 includes a sensor to sense ANS activity. Such a sensor can be used to perform feedback in a closed loop control system. For example, various embodiments sense surrogate parameters, such as respiration and blood pressure, indicative of ANS activity. According to various embodiments, the IMD further includes cardiac stimulation capabilities, such as pacing and defibrillating capabilities in addition to the capabilities to stimulate baroreceptors and/or sense ANS activity.

Figure 9:
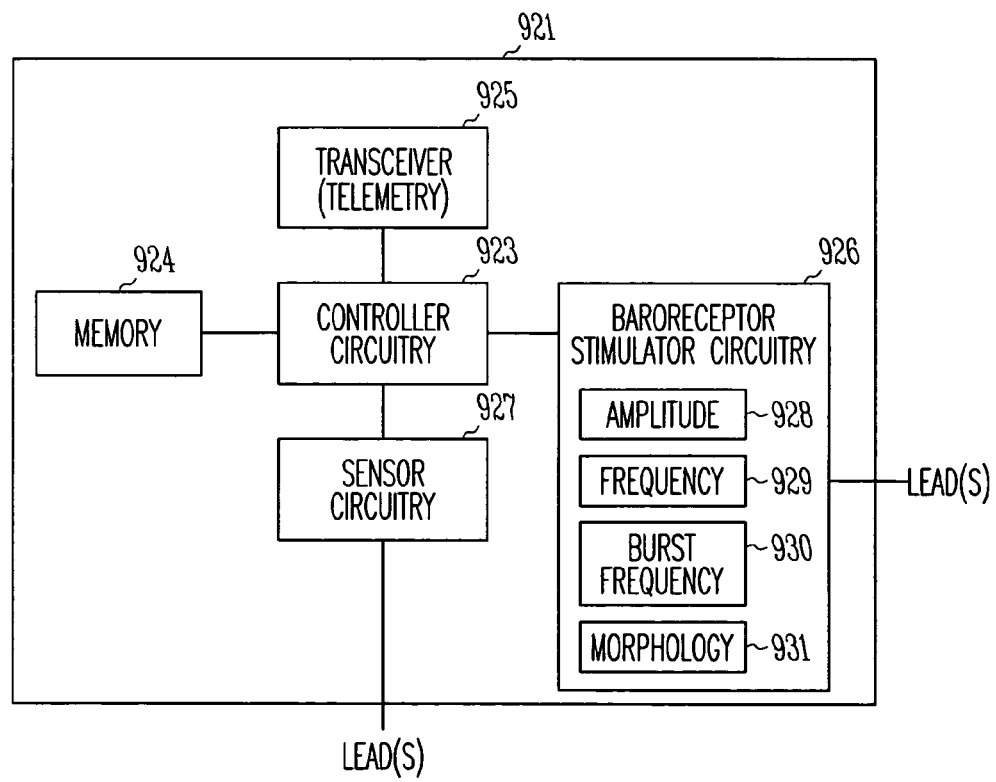
FIG. 9 illustrates an implantable medical device (IMD) such as shown in the system of FIG. 8, according to various embodiments of the present subject matter.

FIG. 9 illustrates an implantable medical device (IMD) 921 such as the IMD 821 shown in the system 820 of FIG. 8, according to various embodiments of the present subject matter. The illustrated IMD 921 performs NS functions. Some embodiments of the illustrated IMD 921 performs an AHT function, and thus illustrates an implantable AHT device. The illustrated device 921 includes controller circuitry 923 and a memory 924. The controller circuitry 923 is capable of being implemented using hardware, software, and combinations of hardware and software. For example, according to various embodiments, the controller circuitry 923 includes a processor to perform instructions embedded in the memory 924 to perform functions associated with NS therapy such as AHT therapy. For example, the illustrated device 921 further includes a transceiver 925 and associated circuitry for use to communicate with a programmer or another external or internal device. Various embodiments have wireless communication capabilities. For example, some transceiver embodiments use a telemetry coil to wirelessly communicate with a programmer or another external or internal device.

The illustrated device 921 further includes baroreceptor stimulation circuitry 926. Various embodiments of the device 921 also includes sensor circuitry 927. One or more leads are able to be connected to the sensor circuitry 927 and baroreceptor stimulation circuitry 926. The baroreceptor stimulation circuitry 926 is used to apply electrical stimulation pulses to desired baroreceptors sites, such as baroreceptor sites in the pulmonary artery, through one or more stimulation electrodes. The sensor circuitry 927 is used to detect and process ANS nerve activity and/or surrogate parameters such as blood pressure, respiration and the like, to determine the ANS activity.

According to various embodiments, the stimulator circuitry 926 includes modules to set any one or any combination of two or more of the following pulse features: the amplitude 928 of the stimulation pulse, the frequency 929 of the stimulation pulse, the burst frequency 930 or duty cycle of the pulse, and the wave morphology 931 of the pulse. Examples of wave morphology include a square wave, triangle wave, sinusoidal wave, and waves with desired harmonic components to mimic white noise such as is indicative of naturally-occurring baroreflex stimulation.

Figure 10A:
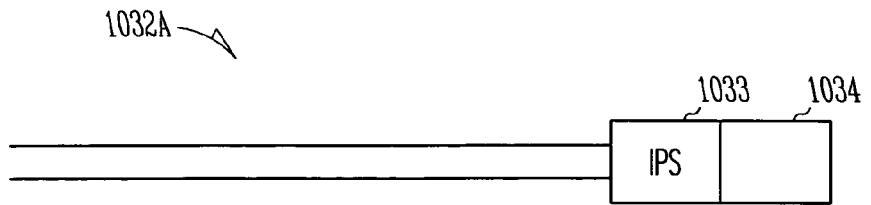
FIGS. 10A-10C illustrate a baroreceptor stimulation lead with an integrated pressure sensor (IPS), according to various embodiments of the present subject matter.
Figure 10B:
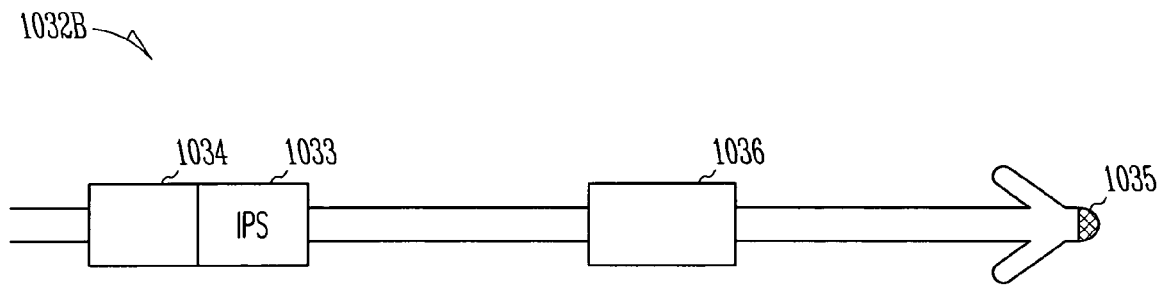
Figure 10C:
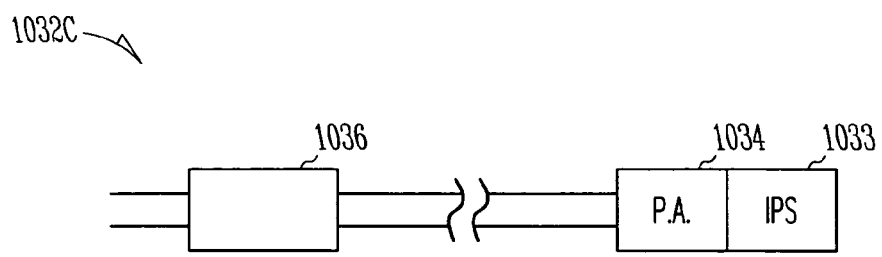

FIGS. 10A-10C illustrate a baroreceptor stimulation lead with an integrated pressure sensor (IPS), according to various embodiments of the present subject matter. Although not drawn to scale, these illustrated leads 1032A, 1032B and 1032C include an IPS 1033 with a baroreceptor stimulator electrode 1034 to monitor changes in blood pressure, and thus the effect of the baroreceptor stimulation. These lead illustrations should not be read as limiting other aspects and embodiments of the present subject matter. In various embodiments, for example, micro-electrical mechanical systems (MEMS) technology is used to sense the blood pressure. Some sensor embodiments determine blood pressure based on a displacement of a membrane.

FIGS. 10A-10C illustrate an IPS on a lead. Some embodiments implant an IPS in an IMD or NS device. The stimulator and sensor functions can be integrated, even if the stimulator and sensors are located in separate leads or positions.

The lead 1032A illustrated in FIG. 10A includes a distally-positioned baroreceptor stimulator electrode 1034 and an IPS 1033. This lead, for example, is capable of being intravascularly introduced to stimulate a baroreceptor site, such as the baroreceptor sites in the pulmonary artery, aortic arch, ligamentum arteriosum, the coronary sinus, in the atrial and ventricular chambers, and/or in cardiac fat pads.

The lead 1032B illustrated in FIG. 10B includes a tip electrode 1035, a first ring electrode 1036, second ring electrode 1034, and an IPS 1033. This lead may be intravascularly inserted into or proximate to chambers of the heart and further positioned proximate to baroreceptor sites such that at least some of the electrodes 1035, 1036 and 1034 are capable of being used to pace or otherwise stimulate the heart, and at least some of the electrodes are capable of stimulating at least one baroreceptor site. The IPS 1033 is used to sense the blood pressure. In various embodiments, the IPS is used to sense the blood pressure in the vessel proximate to the baroreceptor site selected for stimulation.

The lead 1032C illustrated in FIG. 10C includes a distally-positioned baroreceptor stimulator electrode 1034, an IPS 1033 and a ring electrode 1036. This lead 1032C may, for example, be intravascularly inserted into the right atrium and ventricle, and then through the pulmonary valve into the pulmonary artery. Depending on programming in the device, the electrode 1036 can be used to pace and/or sense cardiac activity, such as that which may occur within the right ventricle, and the electrode 1034 and IPS 1033 are located near baroreceptors in or near the pulmonary artery to stimulate and sense, either directly or indirectly through surrogate parameters, baroreflex activity.

Thus, various embodiments of the present subject matter provide an implantable NS device that automatically modulates baroreceptor stimulation using an IPS. Integrating the pressure sensor into the lead provides localized feedback for the stimulation. This localized sensing improves feedback control. For example, the integrated sensor can be used to compensate for inertia of the baroreflex such that the target is not continuously overshot. According to various embodiments, the device monitors pressure parameters such as mean arterial pressure, systolic pressure, diastolic pressure and the like. As mean arterial pressure increases or remains above a programmable target pressure, for example, the device stimulates baroreceptors at an increased rate to reduce blood pressure and control hypertension. As mean arterial pressure decreases towards the target pressure, the device responds by reducing baroreceptor stimulation. In various embodiments, the algorithm takes into account the current metabolic state (cardiac demand) and adjusts neural stimulation accordingly. A NS device having an IPS is able to automatically modulate baroreceptor stimulation, which allows an implantable NS device to determine the level of hypertension in the patient and respond by delivering the appropriate level of therapy. However, it is noted that other sensors, including sensors that do not reside in an NS or neural stimulator device, can be used to provide close loop feedback control.

Figure 11:
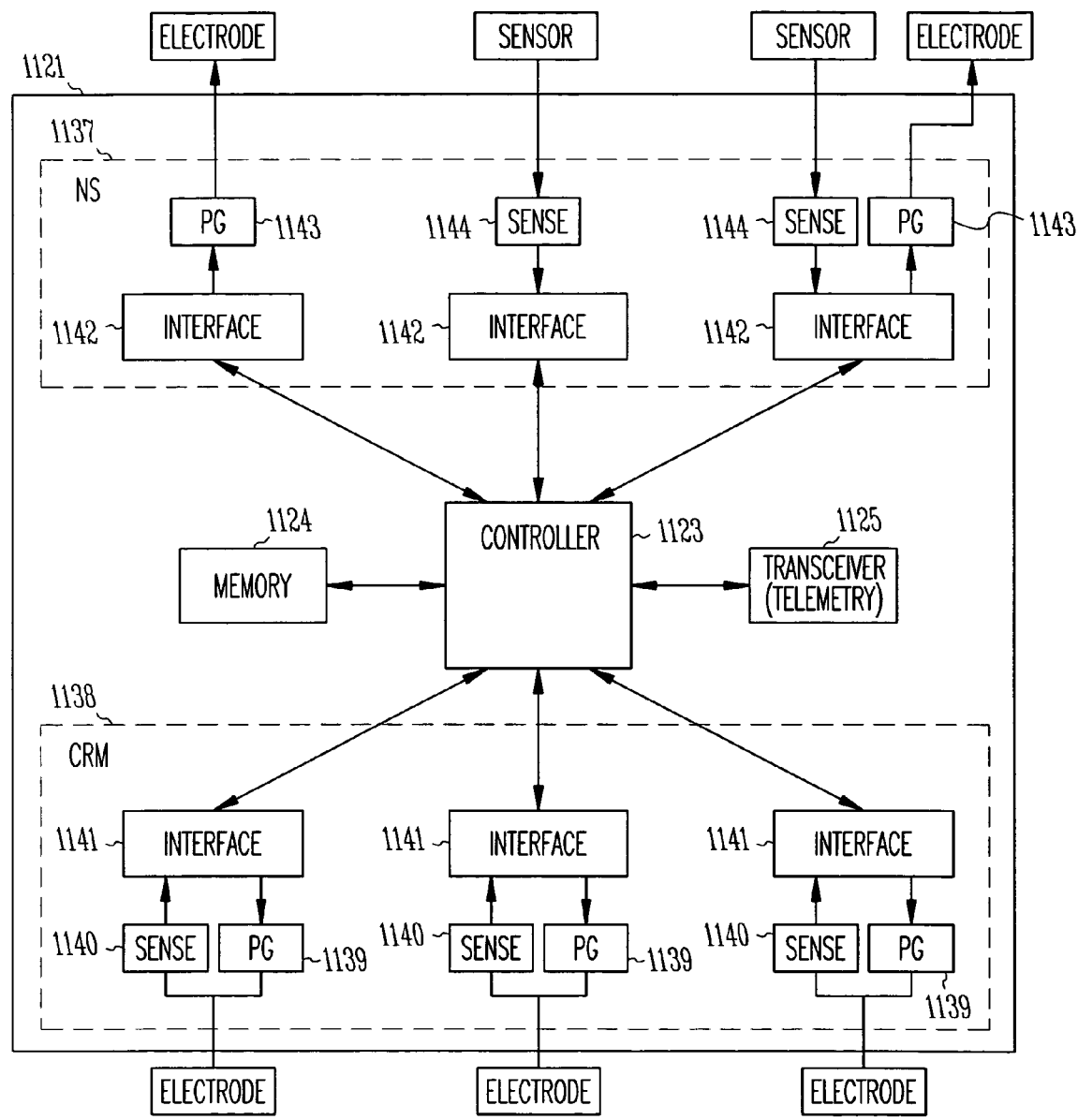
FIG. 11 illustrates an implantable medical device (IMD) such as shown in FIG. 8 having a neural stimulator (NS) component and cardiac rhythm management (CRM) component, according to various embodiments of the present subject matter.

FIG. 11 illustrates an implantable medical device (IMD) 1121 such as shown at 821 in FIG. 8 having an anti-hypertension (AHT) component 1137 and cardiac rhythm management (CRM) component 1138, according to various embodiments of the present subject matter. The illustrated device 1121 includes a controller 1123 and a memory 1124. According to various embodiments, the controller 1123 includes hardware, software, or a combination of hardware and software to perform the baroreceptor stimulation and CRM functions. For example, the programmed therapy applications discussed in this disclosure are capable of being stored as computer-readable instructions embodied in memory and executed by a processor. According to various embodiments, the controller 1123 includes a processor to execute instructions embedded in memory to perform the baroreceptor stimulation and CRM functions. The illustrated device 1121 further includes a transceiver 1125 and associated circuitry for use to communicate with a programmer or another external or internal device. Various embodiments include a telemetry coil.

The CRM therapy section 1138 includes components, under the control of the controller, to stimulate a heart and/or sense cardiac signals using one or more electrodes. The CRM therapy section includes a pulse generator 1139 for use to provide an electrical signal through an electrode to stimulate a heart, and further includes sense circuitry 1140 to detect and process sensed cardiac signals. An interface 1141 is generally illustrated for use to communicate between the controller 1123 and the pulse generator 1139 and sense circuitry 1140. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 1137 includes components, under the control of the controller, to stimulate a baroreceptor and/or sense ANS parameters associated with nerve activity or surrogates of ANS parameters such as blood pressure and respiration. Three interfaces 1142 are illustrated for use to provide ANS therapy. However, the present subject matter is not limited to a particular number interfaces, or to any particular stimulating or sensing functions. Pulse generators 1143 are used to provide electrical pulses to an electrode for use to stimulate a baroreceptor site. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 1144 are used to detect and process signals from a sensor, such as a sensor of nerve activity, blood pressure, respiration, and the like. The interfaces 1142 are generally illustrated for use to communicate between the controller 1123 and the pulse generator 1143 and sense circuitry 1144. Each interface, for example, may be used to control a separate lead. Various embodiments of the NS therapy section only include a pulse generator to stimulate baroreceptors. For example, the NS therapy section provides AHT therapy.

An aspect of the present subject matter relates to a chronically-implanted stimulation system specially designed to treat hypertension by monitoring blood pressure and stimulating baroreceptors to activate the baroreceptor reflex and inhibit sympathetic discharge from the vasomotor center. Baroreceptors are located in various anatomical locations such as the carotid sinus and the aortic arch. Other baroreceptor locations include the pulmonary artery, including the ligamentum arteriosum, and sites in the atrial and ventricular chambers. In various embodiments, the system is integrated into a pacemaker/defibrillator or other electrical stimulator system. Components of the system include a high-frequency pulse generator, sensors to monitor blood pressure or other pertinent physiological parameters, leads to apply electrical stimulation to baroreceptors, algorithms to determine the appropriate time to administer stimulation, and algorithms to manipulate data for display and patient management.

Various embodiments relate to a system that seeks to deliver electrically mediated NS therapy, such as AHT therapy, to patients. Various embodiments combine a "stand-alone" pulse generator with a minimally invasive, unipolar lead that directly stimulates baroreceptors in the vicinity of the heart, such as in the pulmonary artery. This embodiment is such that general medical practitioners lacking the skills of specialist can implant it. Various embodiments incorporate a simple implanted system that can sense parameters indicative of blood pressure. This system adjusts the therapeutic output (waveform amplitude, frequency, etc.) so as to maintain a desired quality of life. In various embodiments, an implanted system includes a pulse generating device and lead system, the stimulating electrode of which is positioned near endocardial baroreceptor tissues using transvenous implant technique(s). Another embodiment includes a system that combines NS therapy with traditional bradyarrhythmia, tachyarrhythmia, and/or congestive heart failure (CHF) therapies. Some embodiments use an additional "baroreceptor lead" that emerges from the device header and is paced from a modified traditional pulse generating system. In another embodiment, a traditional CRM lead is modified to incorporate proximal electrodes that are naturally positioned near baroreceptor sites. With these leads, distal electrodes provide CRM therapy and proximate electrodes stimulate baroreceptors.

A system according to these embodiments can be used to augment partially successful treatment strategies. As an example, undesired side effects may limit the use of some pharmaceutical agents. The combination of a system according to these embodiments with reduced drug doses may be particularly beneficial.

According to various embodiments, the lead(s) and the electrode(s) on the leads are physically arranged with respect to the heart in a fashion that enables the electrodes to properly transmit pulses and sense signals from the heart, and with respect to baroreceptors to stimulate the baroreflex. As there may be a number of leads and a number of electrodes per lead, the configuration can be programmed to use a particular electrode or electrodes. According to various embodiments, the baroreflex is stimulated by stimulating afferent nerve trunks.

Figure 12:
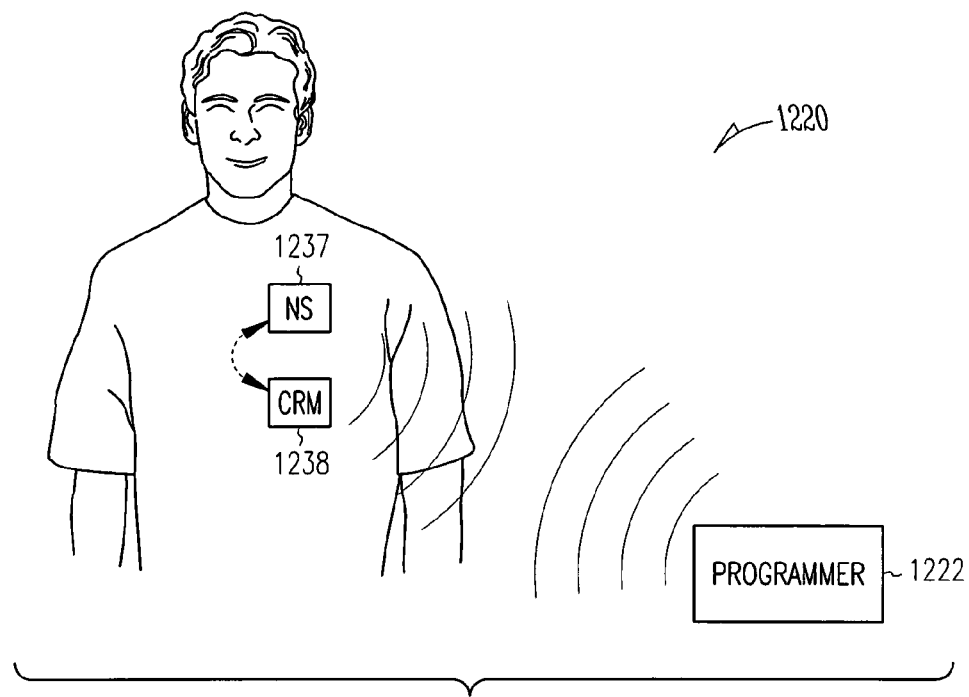
FIG. 12 illustrates a system including a programmer, an implantable neural stimulator (NS) device and an implantable cardiac rhythm management (CRM) device, according to various embodiments of the present subject matter.

FIG. 12 illustrates a system 1220 including a programmer 1222, an implantable neural stimulator (NS) device 1237 and an implantable cardiac rhythm management (CRM) device 1238, according to various embodiments of the present subject matter. Various aspects involve a method for communicating between an NS device 1237, such as an AHT device, and a CRM device 1238 or other cardiac stimulator. In various embodiments, this communication allows one of the devices 1237 or 1238 to deliver more appropriate therapy (i.e. more appropriate NS therapy or CRM therapy) based on data received from the other device. Some embodiments provide on-demand communications. In various embodiments, this communication allows each of the devices 1237 and 1238 to deliver more appropriate therapy (i.e. more appropriate NS therapy and CRM therapy) based on data received from the other device. The illustrated NS device 1237 and the CRM device 1238 are capable of wirelessly communicating with each other, and the programmer is capable of wirelessly communicating with at least one of the NS and the CRM devices 1237 and 1238. For example, various embodiments use telemetry coils to wirelessly communicate data and instructions to each other. In other embodiments, communication of data and/or energy is by ultrasonic means.

In some embodiments, the NS device 1237 stimulates the baroreflex to provide NS therapy, and senses ANS activity directly or using surrogate parameters, such as respiration and blood pressure, indicative of ANS activity. The CRM device 1238 includes cardiac stimulation capabilities, such as pacing and defibrillating capabilities. Rather than providing wireless communication between the NS and CRM devices 1237 and 1238, various embodiments provide a communication cable or wire, such as an intravenously-fed lead, for use to communicate between the NS device 1237 and the CRM device 1238.

Figure 13:
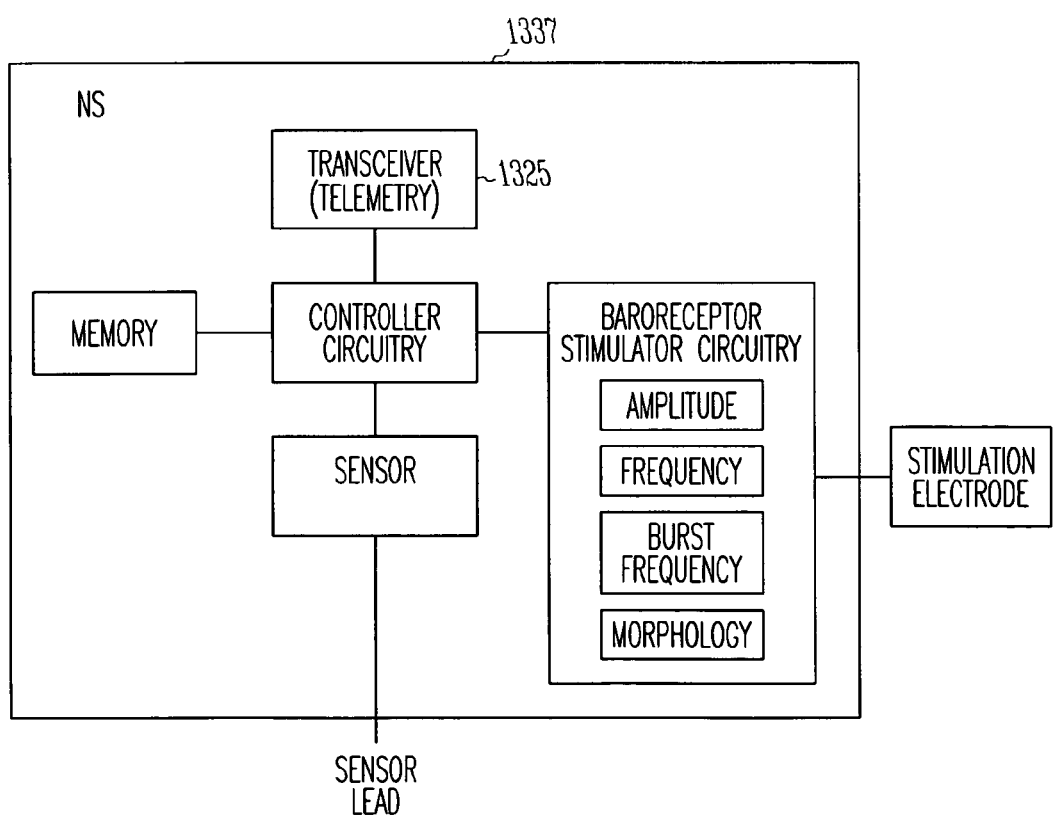
FIG. 13 illustrates an implantable neural stimulator (NS) device such as shown in the system of FIG. 12, according to various embodiments of the present subject matter.
Figure 14:
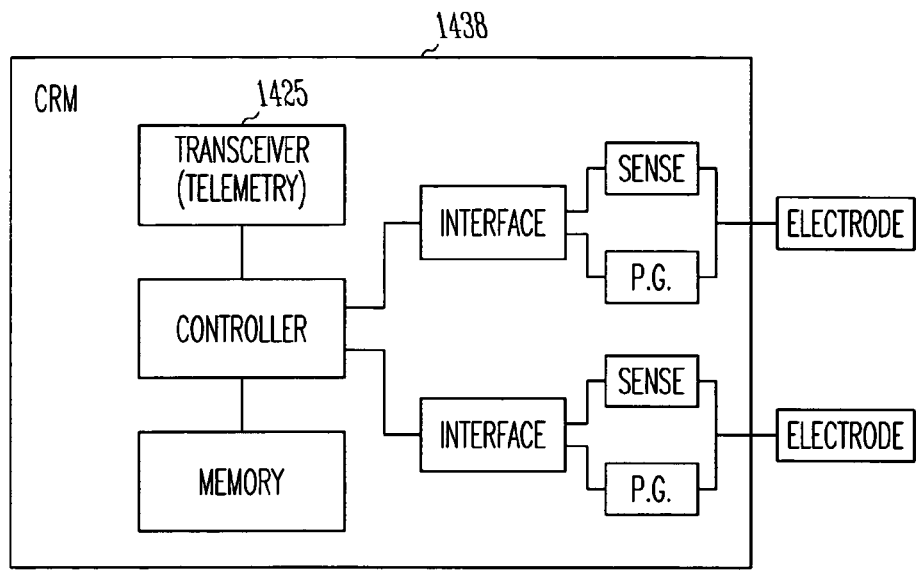
FIG. 14 illustrates an implantable cardiac rhythm management (CRM) device such as shown in the system of FIG. 12, according to various embodiments of the present subject matter.

FIG. 13 illustrates an implantable neural stimulator (NS) device 1337 such as shown at 1237 in the system of FIG. 12, according to various embodiments of the present subject matter. FIG. 14 illustrates an implantable cardiac rhythm management (CRM) device 1438 such as shown at 1238 in the system of FIG. 12, according to various embodiments of the present subject matter. Functions of the components for the NS device 1337 were previously discussed with respect to FIGS. 9 and 11 (the NS component 1137), and functions of the components for the CRM device 1238 were previously discussed with respect to FIG. 11 (the CRM component 1138). In the interest of brevity, these discussions with respect to the NS and CRM functions are not repeated here. Various embodiments of the NS and CRM devices include wireless transceivers 1325 and 1425, respectively, to wirelessly communicate with each other. Various embodiments of the NS and CRM devices include a telemetry coil or ultrasonic transducer to wirelessly communicate with each other.

According to various embodiments, for example, the NS device is equipped with a telemetry coil, allowing data to be exchanged between it and the CRM device, allowing the NS device to modify therapy based on electrophysiological parameters such as heart rate, minute ventilation, atrial activation, ventricular activation, and cardiac events. In addition, the CRM device modifies therapy based on data received from the NS device, such as mean arterial pressure, systolic and diastolic pressure, and baroreceptors stimulation rate.

Some NS device embodiments are able to be implanted in patients with existing CRM devices, such that the functionality of the NS device is enhanced by receiving physiological data that is acquired by the CRM device. The functionality of two or more implanted devices is enhanced by providing communication capabilities between or among the implanted devices. In various embodiments, the functionality is further enhanced by designing the devices to wirelessly communicate with each other.

Figure 15:
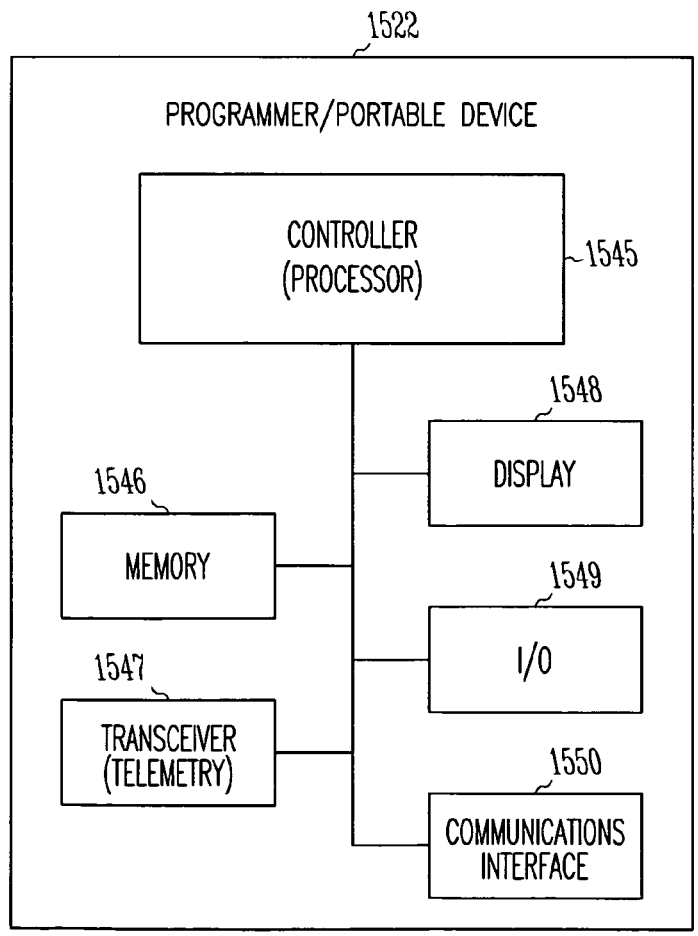
FIG. 15 illustrates a programmer such as illustrated in the systems of FIGS. 8 and 12 or other external device to communicate with the implantable medical device(s), according to various embodiments of the present subject matter.

FIG. 15 illustrates a programmer 1522, such as the programmer 822 and 1222 illustrated in the systems of FIGS. 8 and 12, or other external device to communicate with the implantable medical device(s) 1237 and/or 1238, according to various embodiments of the present subject matter. An example of another external device includes Personal Digital Assistants (PDAs) or personal laptop and desktop computers in an Advanced Patient Management (APM) system. The illustrated device 1522 includes controller circuitry 1545 and a memory 1546. The controller circuitry 1545 is capable of being implemented using hardware, software, and combinations of hardware and software. For example, according to various embodiments, the controller circuitry 1545 includes a processor to perform instructions embedded in the memory 1546 to perform a number of functions, including communicating data and/or programming instructions to the implantable devices. The illustrated device 1522 further includes a transceiver 1547 and associated circuitry for use to communicate with an implantable device. Various embodiments have wireless communication capabilities. For example, various embodiments of the transceiver 1547 and associated circuitry include a telemetry coil for use to wirelessly communicate with an implantable device. The illustrated device 1522 further includes a display 1548, input/output (I/O) devices 1549 such as a keyboard or mouse/pointer, and a communications interface 1550 for use to communicate with other devices, such as over a communication network.

Programmed Therapy Applications

NS and/or CRM functions of a system, whether implemented in two separate and distinct implantable devices or integrated as components into one implantable device, includes processes for performing NS and/or CRM therapy or portions of the therapy. In some embodiments, the NS therapy provides AHT therapy. These processes can be performed by a processor executing computer-readable instructions embedded in memory, for example. These therapies include a number of applications, which have various processes and functions, some of which are identified and discussed below. The processes and functions of these therapies are not necessarily mutually exclusive, as some embodiments of the present subject matter include combinations of two or more of the below-identified processes and functions.

Accounting for Neural Stimulation to Accurately Sense Signals

FIGS. 16A-16D illustrate a system and methods to prevent interference between electrical stimulation from an neural stimulator (NS) device and sensing by a cardiac rhythm management (CRM) device, according to various embodiments of the present subject matter. Neural stimulation is accounted for to improve the ability to sense signals, and thus reduce or eliminate false positives associated with detecting a cardiac event. The NS device includes an AHT device in some embodiments. For example, the NS device communicates with and prevents or otherwise compensates for baroreflex stimulation such that the CRM device does not unintentionally react to the baroreflex stimulation, according to some embodiments. Some embodiments automatically synchronize the baroreflex stimulation with an appropriate refraction in the heart. For example, some systems automatically synchronize stimulation of baroreceptors in or around the pulmonary artery with atrial activation. Thus, the functions of the CRM device are not adversely affected by detecting far-field noise generated by the baroreflex stimulation, even when the baroreflex stimulations are generated near the heart and the CRM sensors that detect the cardiac electrical activation.

Figure 16A:
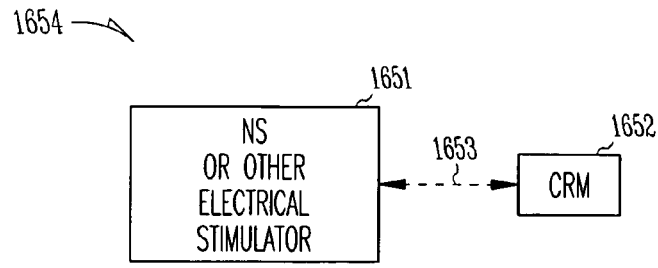
FIGS. 16A-16D illustrate a system and methods to prevent interference between electrical stimulation from a neural stimulator (NS) device and sensing by a cardiac rhythm management (CRM) device, according to various embodiments of the present subject matter.

FIG. 16A generally illustrates a system 1654 that includes NS functions 1651 (such as may be performed by a NS device or a NS component in an integrated NS/CRM device), CRM functions 1652 (such as may be performed by a CRM device or a CRM component in an integrated NS/CRM device) and capabilities to communicate 1653 between the NS and CRM functions. The illustrated communication is bidirectional wireless communication. However, the present subject matter also contemplates unidirectional communication, and further contemplates wired communication. Additionally, the present subject matter contemplates that the NS and CRM functions 1651 and 1652 can be integrated into a single implantable device such that the communication signal is sent and received in the device, or in separate implantable devices. Although baroreflex stimulation as part of neural stimulation is specifically discussed, this aspect of the present subject matter is also applicable to prevent, or account or other wise compensate for, unintentional interference detectable by a sensor and generated from other electrical stimulators.

Figure 16B:
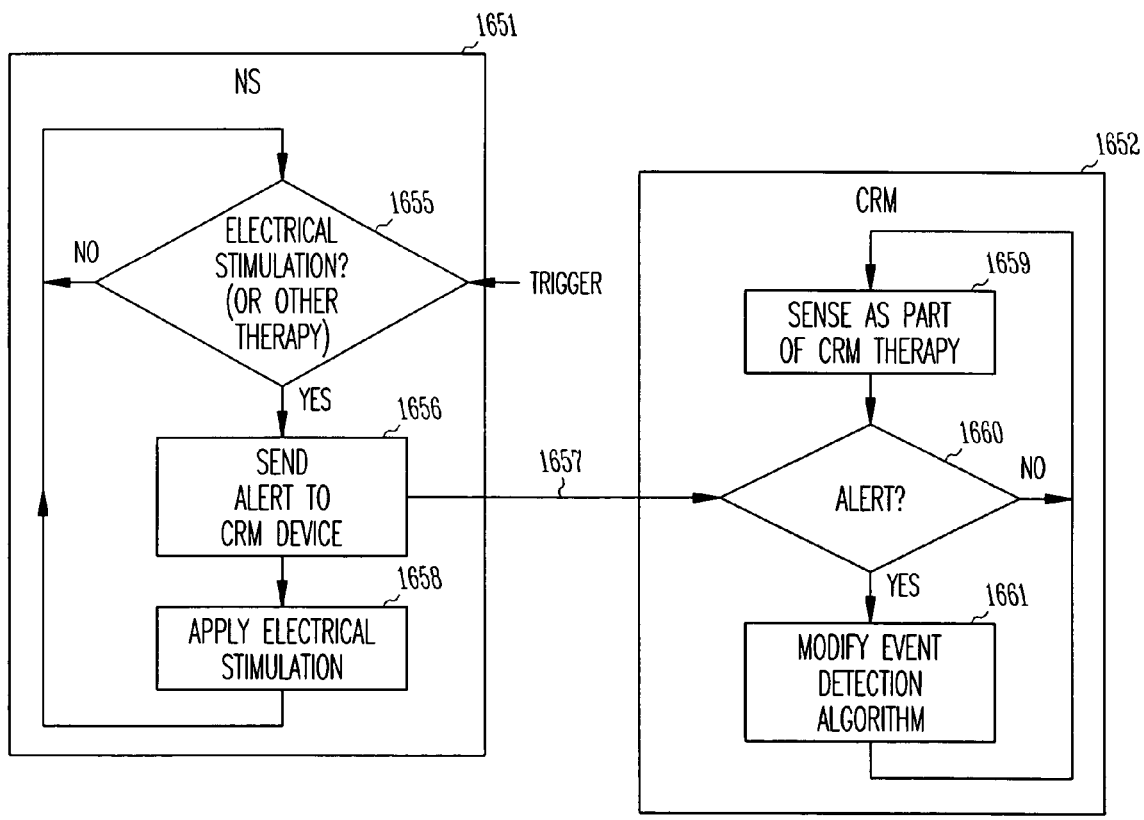

FIG. 16B illustrates a process where CRM functions do not unintentionally react to baroreflex stimulation, according to various embodiments. FIG. 16B illustrates a process where the NS device or component 1651 sends an alert or otherwise informs the CRM device or component when baroreceptors are being electrically stimulated. In the illustrated embodiment, the NS device/component determines at 1655 if electrical stimulation, such as baroreflex stimulation, is to be applied. When electrical stimulation is to be applied, the NS device or component 1651 sends at 1656 an alert 1657 or otherwise informs the CRM device or component 1652 of the electrical stimulation. At 1658, the electrical stimulation is applied by the NS device/component. At 1659 CRM therapy, including sensing, is performed. At 1660, the CRM device/component determines whether an alert 1657 has been received from the NS device/component. If an alert has been received, an event detection algorithm is modified at 1661 to raise a detection threshold, provide a blackout or blanking window, or otherwise prevent the electrical stimulation in the NS device or component from being misinterpreted as an event by the CRM device/component.

Figure 16C:
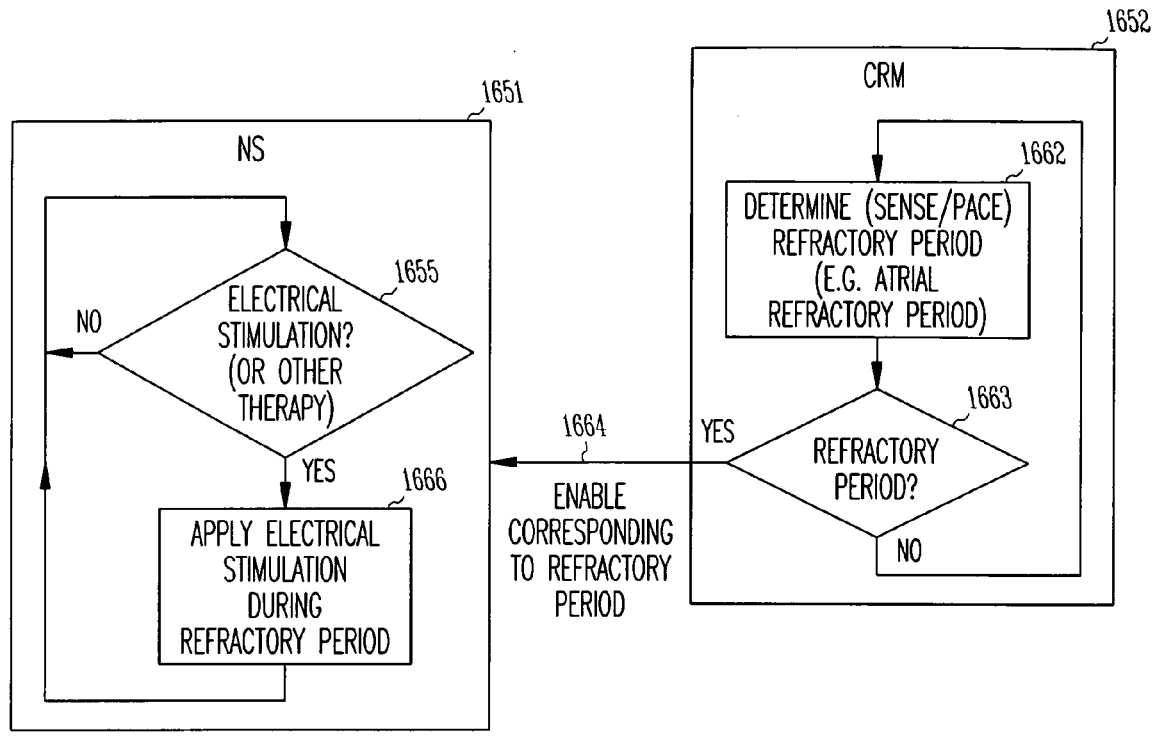
Figure 16D:
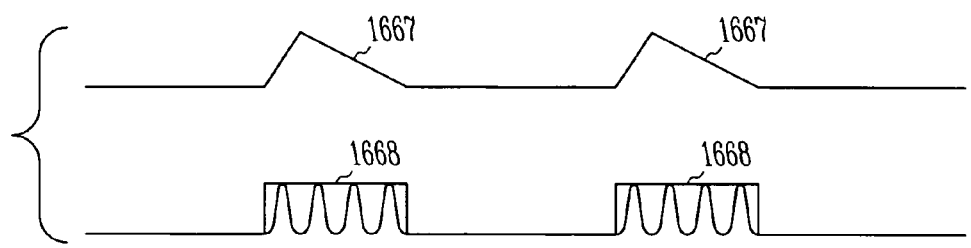

FIG. 16C illustrates a process where CRM functions do not unintentionally react to baroreflex stimulation, according to various embodiments. The CRM device/component 1652 determines a refractory period for the heart at 1662. At 1663, if a refractory period is occurring or is expected to occur in a predictable amount of time, an enable 1664 corresponding to the refractory is provided to the NS device/component 1651. The AHT device/component 1651 determines if electrical stimulation is desired at 1655. When desired, the AHT device/component applies electrical stimulation during a refractory period at 1666, as controlled by the enable signal 1664. FIG. 16D illustrates a refractory period at 1667 in a heart and a baroreflex stimulation 1668, and further illustrates that baroreflex stimulation is applied during the refractory period.

A refractory period includes both absolute and relative refractory periods. Cardiac tissue is not capable of being stimulated during the absolute refractory period. The required stimulation threshold during an absolute refractory period is basically infinite. The relative refractory period occurs after the absolute refractory period. During the relative refractory period, as the cardiac tissue begins to repolarize, the stimulation threshold is initially very high and drops to a normal stimulation threshold by the end of the relative refractory period. Thus, according to various embodiments, a neural stimulator applies neural stimulation during either the absolute refractory period or during a portion of the relative refractory period corresponding a sufficiently high stimulation threshold to prevent the neural stimulation from capturing cardiac tissue.

Various embodiments of the present subject matter relate to a method of sensing atrial activation and confining pulmonary artery stimulation to the atrial refractory period, preventing unintentional stimulation of nearby atrial tissue. An implantable baroreceptor stimulation device monitors atrial activation with an atrial sensing lead. A lead in the pulmonary artery stimulates baroreceptors in the vessel wall. However, instead of stimulating these baroreceptors continuously, the stimulation of baroreceptors in the pulmonary artery occurs during the atrial refractory period to avoid capturing nearby atrial myocardium, maintaining the intrinsic atrial rate and activation. Various embodiments of the present subject matter combine an implantable device for stimulating baroreceptors in the wall of the pulmonary artery with the capability for atrial sensing. Various embodiments stimulate baroreceptors in the cardiac fat pads, in the heart chambers, and/or afferent nerves.

Figure 17:
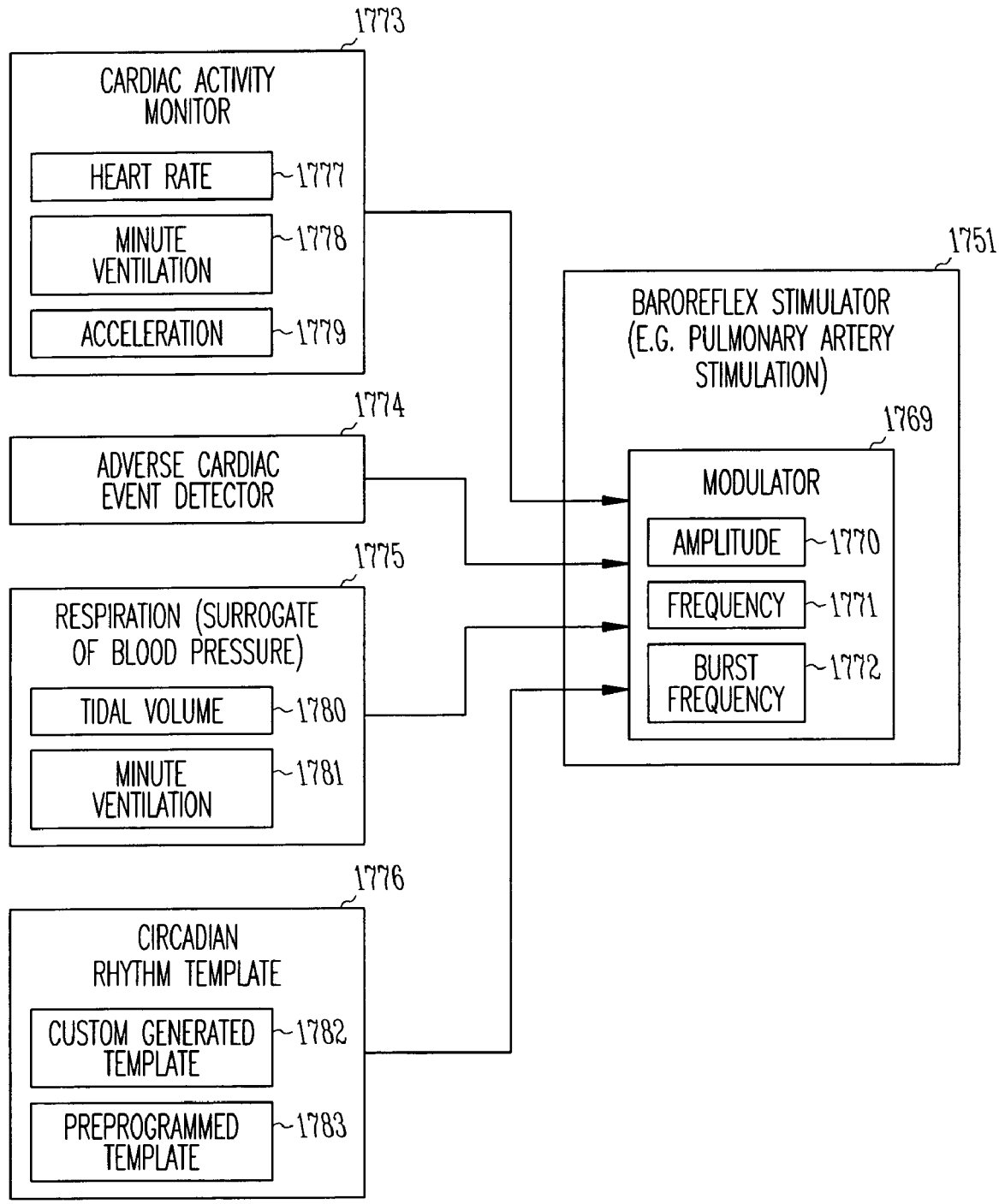
FIG. 17 illustrates a system to modulate baroreflex stimulation, according to various embodiments of the present subject matter.

FIG. 17 illustrates a system to modulate baroreflex stimulation, according to various embodiments of the present subject matter. The illustrated system includes a baroreflex stimulator 1751, such as stimulator to stimulate baroreceptors in and around the pulmonary artery. The baroreflex stimulator can be included in a stand-alone NS device or as a NS component in an integrated NS/CRM device, for example. The illustrated stimulator 1751 includes a modulator 1769 for use to selectively increase and decrease the applied baroreflex stimulation. According to various embodiments, the modulator 1769 includes any one of the following modules: a module 1770 to change the amplitude of the stimulation pulse; a module 1771 to change the frequency of the stimulation pulse; and a module 1772 to change the burst frequency of the stimulation pulse. The burst frequency can also be referred to as a duty cycle. According to various embodiments, the modulator 1769 includes functions for the various combinations of two or more of the modules 1770, 1771 and 1772. Additionally, a stimulator can include a waveform generator capable of providing different waveforms in response to a control signal.

Various embodiments of the system include any one or any combination of a cardiac activity monitor 1773, an adverse event detector 1774, a respiration monitor 1775, and a circadian rhythm template 1776 which are capable of controlling the modulator 1769 of the stimulator 1751 to appropriately apply a desired level of baroreflex stimulation. Each of these 1773, 1774, 1775, and 1776 are associated with a method to modulate a baroreflex signal. According to various embodiments, the system includes means to modulate a baroreflex signal based on the following parameters or parameter combinations: cardiac activity (1773); an adverse event (1774); respiration (1775); circadian rhythm (1776); cardiac activity (1773) and an adverse event (1774); cardiac activity (1773) and respiration (1775); cardiac activity (1773) and circadian rhythm (1776); an adverse event (1774) and respiration (1775); an adverse event (1774) and circadian rhythm (1776); respiration (1775) and circadian rhythm (1776); cardiac activity (1773), an adverse event (1774), and respiration (1775); cardiac activity (1773), an adverse event (1774), and circadian rhythm (1776); cardiac activity (1773), respiration (1775), and circadian rhythm (1776); an adverse event (1774), respiration (1775) and circadian rhythm (1776); and cardiac activity (1773), an adverse event (1774), respiration (1775) and circadian rhythm (1776).

The stimulation can be applied to an afferent nerve trunk such as the vagal nerve using a cuff electrode or an intravascularly-fed lead positioned proximate to the nerve trunk. The stimulation can be applied to baroreceptor sites such are located in the pulmonary artery, aortic arch, and carotid sinus, for example, using intravenously-fed leads. The stimulation can be applied to baroreceptor sites located in cardiac fat pads using intravenously-fed leads or by screwing electrodes into the fat pads. Embodiments of the cardiac activity detector 1774, for example, include any one or any combination of a heart rate monitor 1777, a minute ventilation monitor 1778, and an acceleration monitor 1779. The respiration monitor 1775 functions as a surrogate for monitoring blood pressure. Embodiments of the respiration monitor 1775 include any one or any combination of a tidal volume monitor 1780 and a minute ventilation module 1781. Embodiments of the circadian rhythm template 1776 include any one or combination of a custom generated template 1782 and a preprogrammed template 1783. These embodiments are discussed in more detail below with respect to FIGS. 18A-18C, 19A-19B, 20A-20B, 21A-21E, 22 and 23A-23C.

Various embodiments use the circadian rhythm template to provide AHT therapy. Various embodiments use the circadian rhythm template to provide apnea therapy.

Modulation of Baroreflex Stimulation Based on Systolic Intervals

Activation of the sympathetic or parasympathetic nervous systems is known to alter certain systolic intervals, primarily the pre-ejection period (PEP), the time interval between sensed electrical activity within the ventricle (e.g. sensing of the "R" wave) and the onset of ventricular ejection of blood. The PEP may be measured from the sensed electrical event to the beginning of pressure increase in the pulmonary artery, using a pulmonary arterial pressure sensor, or may be measured to the beginning of an increase in intracardiac impedance, accompanying a decrease in ventricular volume during ejection, using electrodes positioned in the right or spanning the left ventricle. At rest, as determined by heart rate or body activity measured with an accelerometer for example, neural stimulation is modulated to maintain PEP in a pre-programmed range. A sudden decrease in PEP indicates an increase in sympathetic tone associated with exercise or emotional stress. This condition may be used to decrease neural stimulation permitting increases in heart rate and contractility necessary to meet metabolic demand. In like manner, a subsequent dramatic lengthening of PEP marks the end of increased metabolic demand. At this time control of blood pressure with neural stimulation could recommence.

Modulation of Baroreflex Stimulation Based on Cardiac Activity

The present subject matter describes a method of automatically modulating baroreceptor stimulation based on cardiac activity, such as can be determined by the heart rate, minute ventilation, acceleration and combinations thereof. The functionality of a device for electrically stimulating baroreceptors is enhanced by applying at least a relatively high baropacing rate during rest when metabolic demand is relatively low, and progressively less baropacing during physical exertion as metabolic demand increases. Indices of cardiac activity are used to automatically modulate the electrical stimulation of baroreceptors, allowing an implantable anti-hypertension device to respond to changes in metabolic demand. According to various embodiments, a CRM device, such as a pacemaker, AICD or CRT devices, also has a baroreceptor stimulation lead. The device monitors cardiac activity through existing methods using, for example, a blended sensor. A blended sensor includes two sensors to measure parameters such as acceleration and minute ventilation. The output of the blended sensor represents a composite parameter. Various NS and AHT therapies use composite parameters derived from two or more sensed parameters as discussed within this disclosure. At rest (lower cardiac activity) the device stimulates baroreceptors at a higher rate, reducing blood pressure and controlling hypertension. As cardiac activity increases, the device responds by temporarily reducing baroreceptor stimulation. This results in a temporary increase in blood pressure and cardiac output, allowing the body to respond to increased metabolic demand. For example, some embodiments provide baroreflex stimulation during rest and withdraw baroreflex stimulation during exercise to match normal blood pressure response to exercise. A pressure transducer can be used to determine activity. Furthermore, activity can be sensed using sensors that are or have been used to drive rate adaptive pacing. Examples of such sensors include sensor to detect body movement, heart rate, QT interval, respiration rate, transthoracic impedance, tidal volume, minute ventilation, body posture, electroencephalogram (EEG), electrocardiogram (ECG), electrooculogram (EOG), electromyogram (EMG), muscle tone, body temperature, pulse oximetry, time of day and pre-ejection interval from intracardiac impedance.

Various embodiments of the cardiac activity monitor includes a sensor to detect at least one pressure parameter such as a mean arterial parameter, a pulse pressure determined by the difference between the systolic and diastolic pressures, end systolic pressure (pressure at the end of the systole), and end diastolic pressure (pressure at the end of the diastole). Various embodiments of the cardiac activity monitor include a stroke volume monitor. Heart rate and pressure can be used to derive stroke volume. Various embodiments of the cardiac activity monitor use at least one electrogram measurement to determine cardiac activity. Examples of such electrogram measurements include the R-R interval, the P-R interval, and the QT interval. Various embodiments of the cardiac activity monitor use at least one electrocardiogram (ECG) measurement to determine cardiac activity.

Figure 18A:
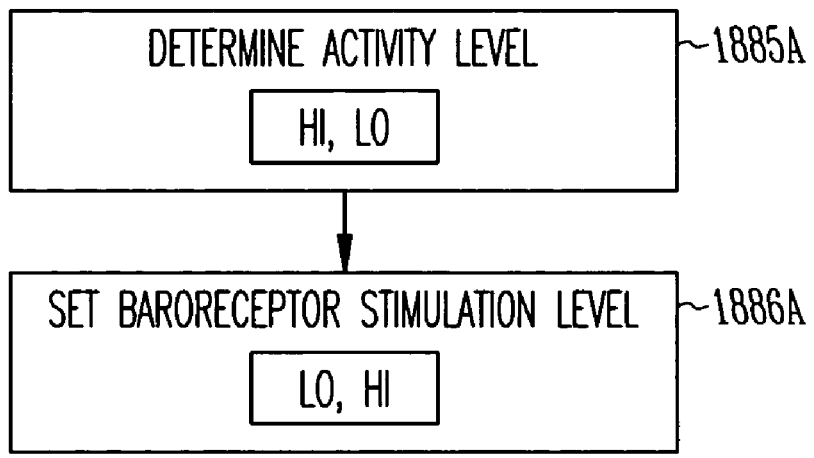
FIGS. 18A-18C illustrate methods for modulating baroreceptor stimulation based on a cardiac activity parameter, according to various embodiments of the present subject matter.
Figure 18B:
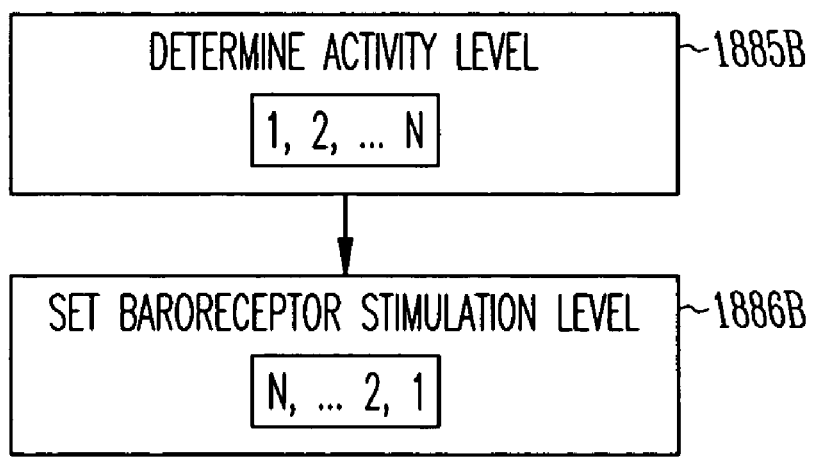
Figure 18C:
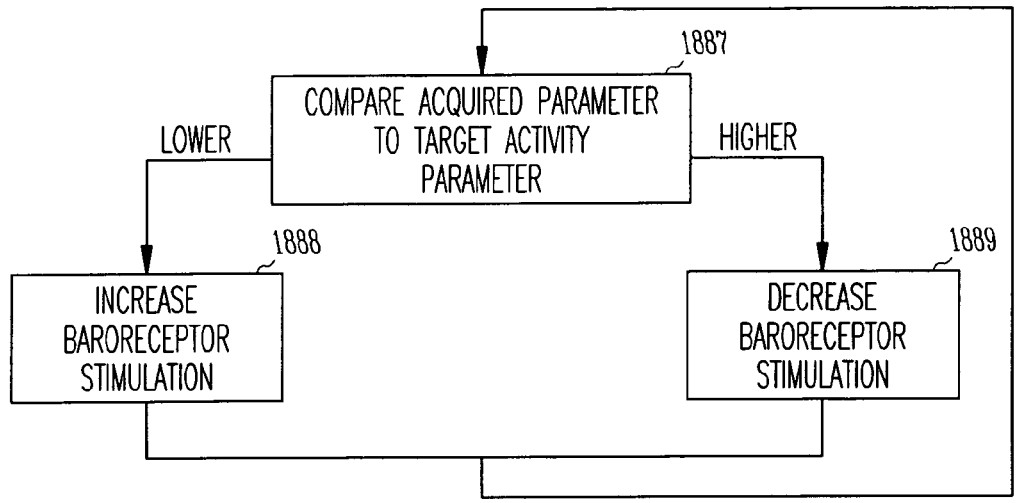

FIGS. 18A-18C illustrate methods for modulating baroreceptor stimulation based on a cardiac activity parameter, according to various embodiments of the present subject matter. The cardiac activity can be determined by a CRM device, an NS device, or an implantable device with NS/CRM capabilities. A first process 1884A for modulating baroreceptor stimulation based on cardiac activity is illustrated in FIG. 18A. At 1885A the activity level is determined. According to various embodiments, the determination of activity level is based on heart rate, minute ventilation, acceleration or any combination of heart rate, minute ventilation, acceleration. In the illustrated process, the activity level has two defined binary levels (e.g. HI and LO). In some embodiments, the LO level includes no stimulation. It is determined whether the activity level is HI or LO. At 1886A, the baroreceptor stimulation level is set based on the determined activity level. A LO stimulation level is set if the activity level is determined to be HI, and a HI stimulation level is set if the activity level is determined to be LO.

A second process 1884B for modulating baroreceptor stimulation based on cardiac activity is illustrated in FIG. 18B. At 1885B the activity level is determined. According to various embodiments, the determination of activity level is based on heart rate, minute ventilation, acceleration or any combination of heart rate, minute ventilation, acceleration. In the illustrated process, the activity level has more than two defined levels or n defined levels. It is determined whether the activity level is level 1, level 2 . . . or level n. The activity level labels correspond to an increasing activity. At 1886B, the baroreceptor stimulation level is set based on the determined activity level. Available stimulation levels include level n . . . level 2 and level 1, where the stimulation level labels correspond to increasing stimulation. According to various embodiments, the selected baroreceptor stimulation level is inversely related to the determined activity level. For example, if it is determined that the cardiac activity level is at the highest level n, then the stimulation level is set to the lowest level n. If it determined that the stimulation level is at the first or second to the lowest level, level 1 or level 2 respectively, then the stimulation level is set to the first or second to the highest level, level 1 or level 2 respectively.

Another process 1884C for modulating baroreceptor stimulation based on cardiac activity is illustrated in FIG. 18C. At 1887, an acquired cardiac activity parameter is compared to a target activity parameter. If the acquired cardiac activity is lower than the target activity parameter, baroreceptor stimulation is increased at 1888. If the acquired cardiac activity is higher than the target activity parameter, baroreceptor stimulation is decreased at 1889.

An aspect of the present subject matter relates to a method of automatically modulating the intensity of baroreceptor stimulation based on respiration, as determined by tidal volume or minute ventilation. Instead of applying continuous baroreceptor stimulation, the NS device monitors the level of hypertension and delivers an appropriate level of therapy, using respiration as a surrogate for blood pressure, allowing the device to modulate the level of therapy. The present subject matter uses indices of respiration, such as impedance, to determined tidal volume and minute ventilation and to automatically modulate baroreceptor stimulation. Thus, an implantable NS device is capable of determining the level of hypertension in the patient and respond by delivering an appropriate level of therapy. In various embodiments, an implantable NS device contains a sensor to measure tidal volume or minute ventilation. For example, various embodiments measure transthoracic impedance to obtain a rate of respiration. The device receives this data from a CRM device in some embodiments. The NS device periodically monitors these respiration parameters. As respiration decreases or remains below a programmable target, the device stimulates baroreceptors at an increased rate, reducing blood pressure and controlling hypertension. As mean arterial pressure increases towards the target, the device responds by reducing baroreceptor stimulation. In this way, the AHT device continuously delivers an appropriate level of therapy.

Figure 19A:
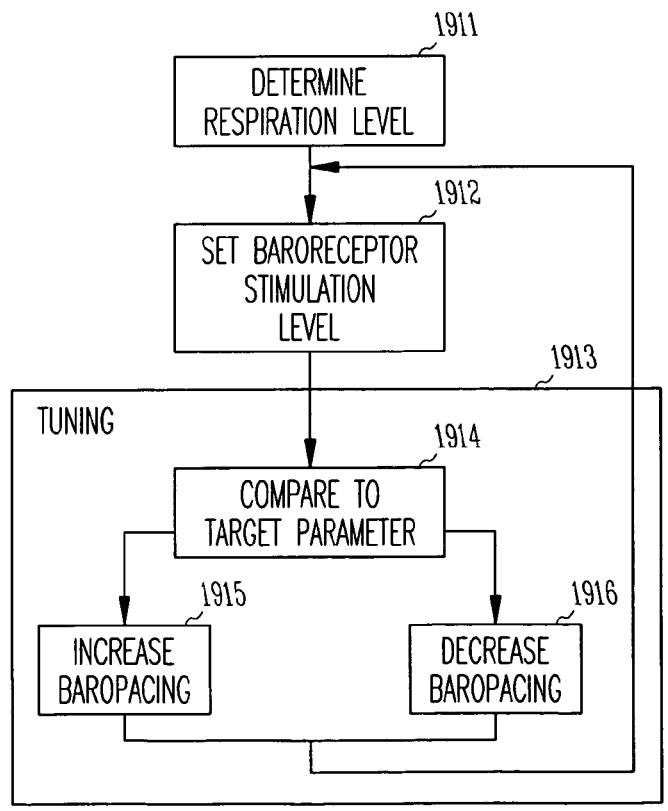
FIGS. 19A-19B illustrate methods for modulating baroreceptor stimulation based on a respiration parameter, according to various embodiments of the present subject matter.
Figure 19B:
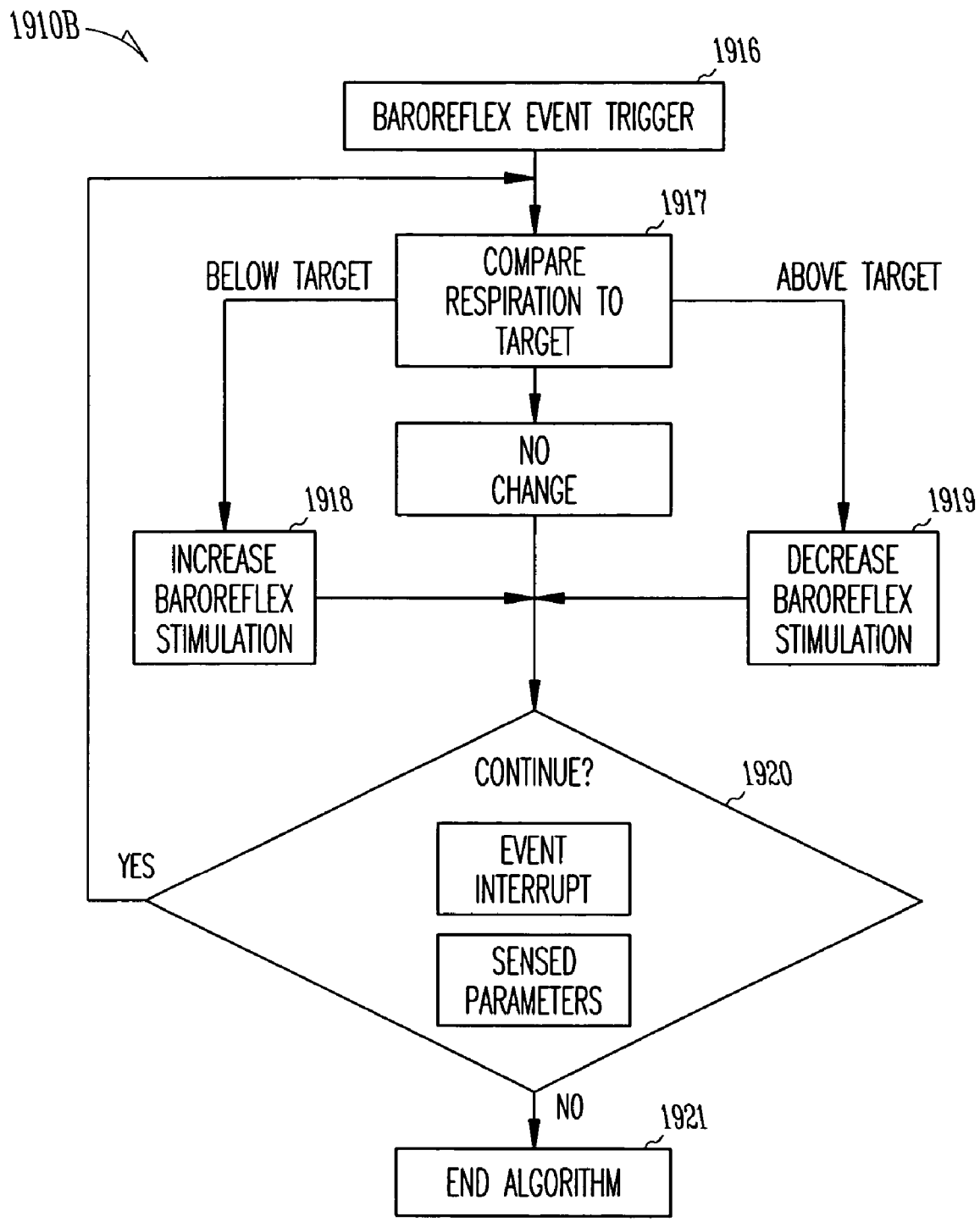

FIGS. 19A-19B illustrate methods for modulating baroreceptor stimulation based on a respiration parameter, according to various embodiments of the present subject matter. The respiration parameter can be determined by a CRM device, an NS device, or an implantable device with NS/CRM capabilities. One embodiment of a method for modulating baroreceptor stimulation based on a respiration parameter is illustrated at 1910A in FIG. 19A. The respiration level is determined at 1911, and the baroreceptor stimulation level is set at 1912 based on the determined respiration level. According to various embodiments, the desired baropacing level is tuned at 1913. For example, one embodiment compares an acquired parameter to a target parameter at 1914. The baropacing can be increased at 1915 or decreased at 1916 based on the comparison of the acquired parameter to the target parameter.

One embodiment of a method for modulating baroreceptor stimulation based on a respiration parameter is illustrated at 1910B in FIG. 19B. At 1916, a baroreflex event trigger occurs, which triggers an algorithm for a baroreflex stimulation process. At 1917, respiration is compared to a target parameter. Baroreflex stimulation is increased at 1918 if respiration is below the target and is decreased at 1919 if respiration is above the target. According to various embodiments, the stimulation is not changed if the respiration falls within a blanking window. Various embodiments use memory to provide a hysteresis effect to stabilize the applied stimulation and the baroreflex response. Additionally, in various embodiments, the respiration target is modified during the therapy based on various factors such as the time of day or activity level. At 1920, it is determined whether to continue with the baroreflex therapy algorithm based on, for example, sensed parameters or the receipt of an event interrupt. If the baroreflex algorithm is to continue, then the process returns to 1917 where respiration is again compared to a target parameter; else the baroreflex algorithm is discontinued at 1921.

Modulation of Baroreflex Stimulation Based on Adverse Event

Aspects of the present subject matter include a method of automatically increasing baroreceptor stimulation upon detection of an adverse cardiac event to increase vasodilatory response and potentially prevent or reduce myocardial ischemic damage. Various embodiments include a feedback mechanism in a cardiac rhythm management device (such as a pacemaker, AICD or CRT device), which also has a stimulation lead for electrically stimulating baroreceptors. The device monitors cardiac electrical activity through existing methods. In the event of an adverse cardiac event such as ventricular fibrillation (VF) and atrial fibrillation (AF), ventricular tachycardia (VT) and atrial tachycardia (AT) above a predefined rate, and dyspnea as detected by a minute ventilation sensor, angina, decompensation and ischemia, the device responds by increasing baroreceptors stimulation to the maximally allowable level. As a result, blood pressure is temporarily lowered, potentially preventing or reducing myocardial damage due to ischemia. The functionality of a device to treat hypertension can be expanded if it can respond to adverse cardiac events by temporarily modulating the extent of baroreceptors stimulation. Event detection algorithms automatically modulate baroreceptors stimulation, allowing an implantable AHT device to respond to an adverse event by increasing baroreceptors stimulation, potentially preventing or reducing myocardial ischemic damage.

Figure 20A:
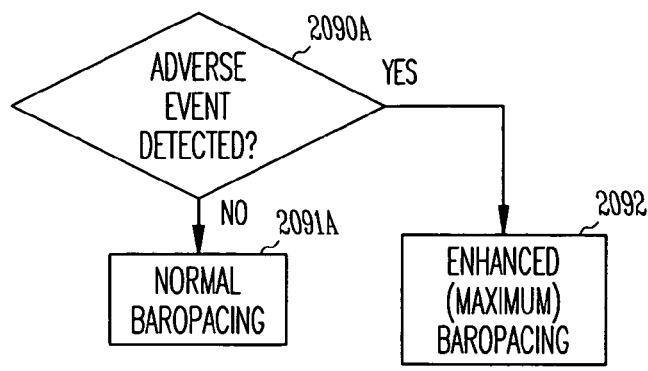
FIGS. 20A-20B illustrate methods for modulating baroreceptor stimulation based on detection of an adverse event, according to various embodiments of the present subject matter.
Figure 20B:
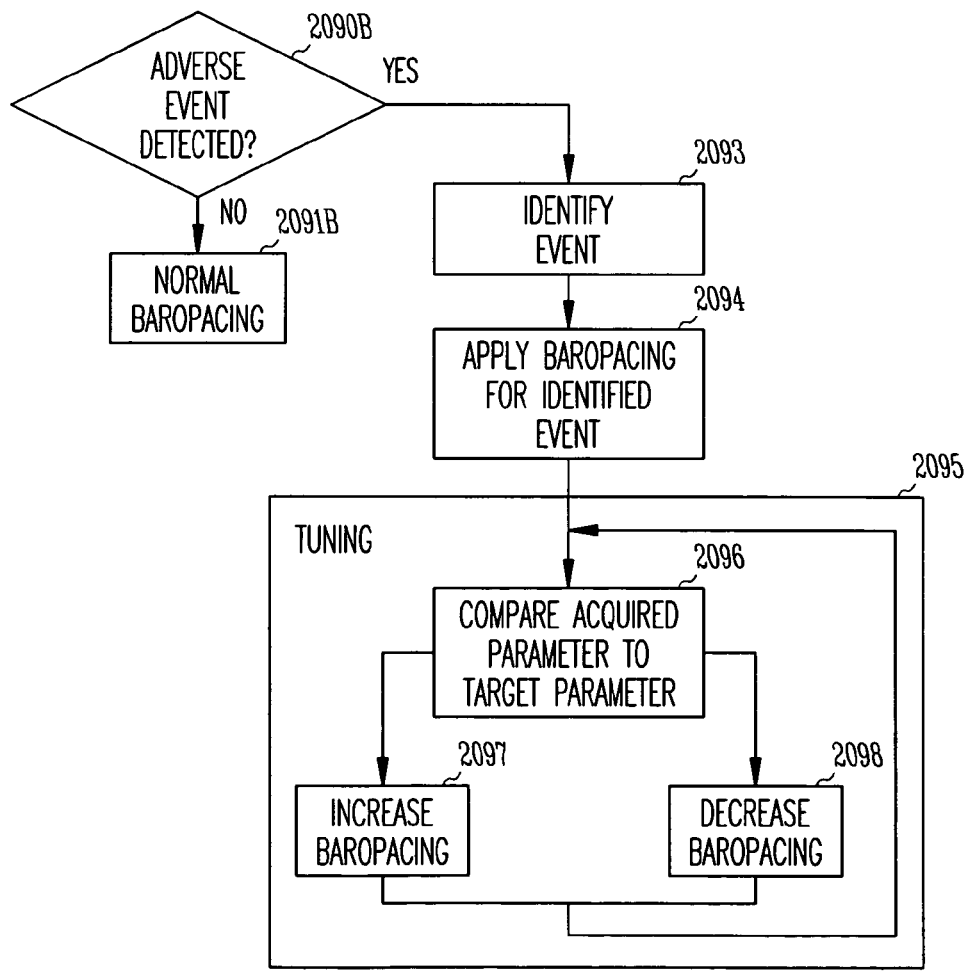

FIGS. 20A-20B illustrate methods for modulating baroreceptor stimulation based on detection of an adverse event, according to various embodiments of the present subject matter. The adverse event can be determined by a CRM device, an NS device, or an implantable device with NS/CRM capabilities. FIG. 20A illustrates one embodiment for modulating baroreceptor stimulation based on detection of an adverse event. At 2090A, it is determined whether an adverse event has been detected. If an adverse event has not been detected, normal baropacing (baropacing according to a normal routine) is performed at 2091A. If an adverse event has been detected, enhanced baropacing is performed at 2092. In various embodiments, the maximum allowable baropacing is performed when an adverse event is detected. Other baropacing procedures can be implemented. For example, various embodiments normally apply baropacing stimulation and withholds baropacing therapy when an adverse event is detected, and various embodiments normally withhold baropacing therapy and apply baropacing stimulation when an adverse event is detected. FIG. 20B illustrate on embodiment for modulating baroreceptor stimulation based on detection of an adverse event. At 2090B, it is determined whether an adverse event has been detected. If an adverse event has not been detected, normal baropacing (baropacing according to a normal routine) is performed at 2091B. If an adverse event has been detected, the event is identified at 2093, and the appropriate baropacing for the identified adverse event is applied at 2094. For example, proper blood pressure treatment may be different for ventricular fibrillation than for ischemia. According to various embodiments, the desired baropacing is tuned for the identified event at 2095. For example, one embodiment compares an acquired parameter to a target parameter at 2096. The baropacing can be increased at 2097 or decreased at 2098 based on the comparison of the acquired parameter to the target parameter.

According to various embodiments, an adverse event includes detectable precursors, such that therapy can be applied to prevent cardiac arrhythmia. In some embodiments, an adverse event includes both cardiac events and non-cardiac events such as a stroke. Furthermore, some embodiments identify both arrhythmic and non-arrhythmic events as adverse events.

Modulation of Baroreflex Stimulation Based on Circadian Rhythm

An aspect of the present subject matter relates to a method for stimulating the baroreflex in hypertension patients so as to mimic the natural fluctuation in blood pressure that occurs over a 24-hour period. Reflex reduction in hypertension is achieved during long-term baroreceptor stimulation without altering the intrinsic fluctuation in arterial pressure. According to various embodiments, an implantable device is designed to stimulate baroreceptors in the carotid sinus, pulmonary artery, or aortic arch using short, high-frequency bursts (such as a square wave with a frequency within a range from approximately 20-150 Hz), for example. Some embodiments directly stimulate the carotid sinus nerve, aortic nerve or vagus nerve with a cuff electrode. However, the bursts do not occur at a constant rate. Rather the stimulation frequency, amplitude, and/or burst frequency rises and falls during the day mimicking the natural circadian rhythm.

Thus, various embodiments of a NS device accounts for natural fluctuations in arterial pressure that occur in both normal and hypertensive individuals. Aside from activity-related changes in mean arterial pressure, subjects also exhibit a consistent fluctuation in pressure on a 24-hour cycle. A device which provides periodic baroreceptor stimulation mimics the intrinsic circadian rhythm, allowing for reflex inhibition of the systematic nervous system and reduced systemic blood pressure without disturbing this rhythm. The present subject matter provides a pacing protocol which varies the baroreceptor stimulation frequency/amplitude in order to reduce mean arterial pressure without disturbing the intrinsic circadian rhythm.

Figure 21A:
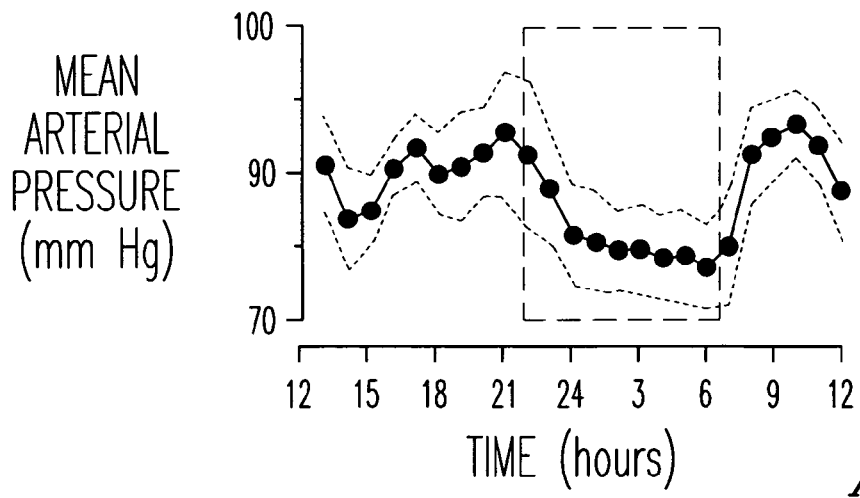
FIGS. 21A-21E illustrate circadian rhythm.
Figure 21B:
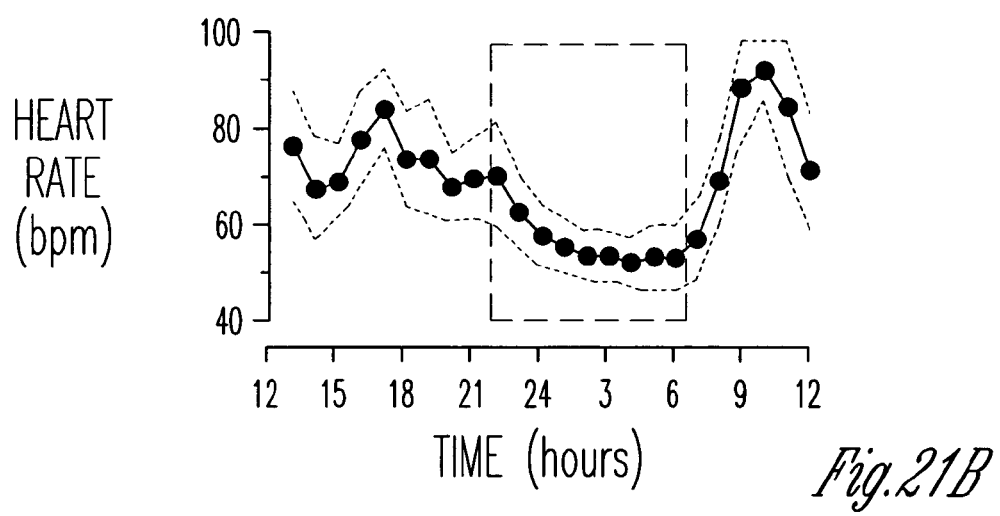
Figure 21C:
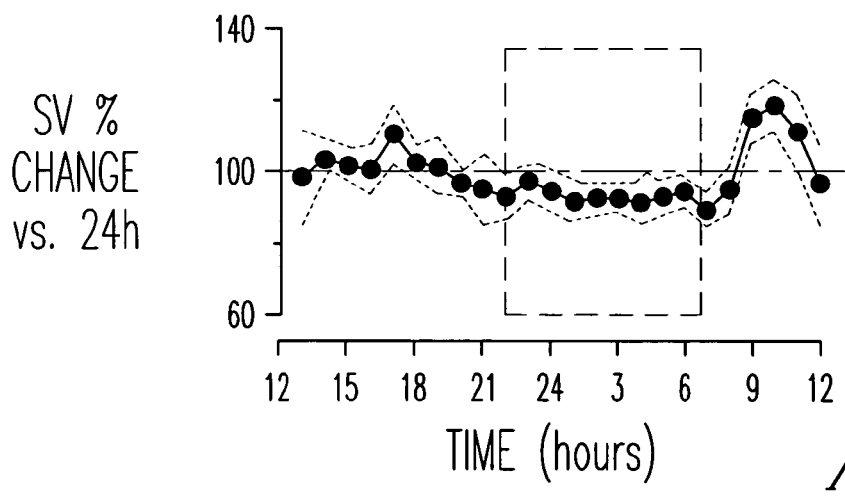
Figure 21D:
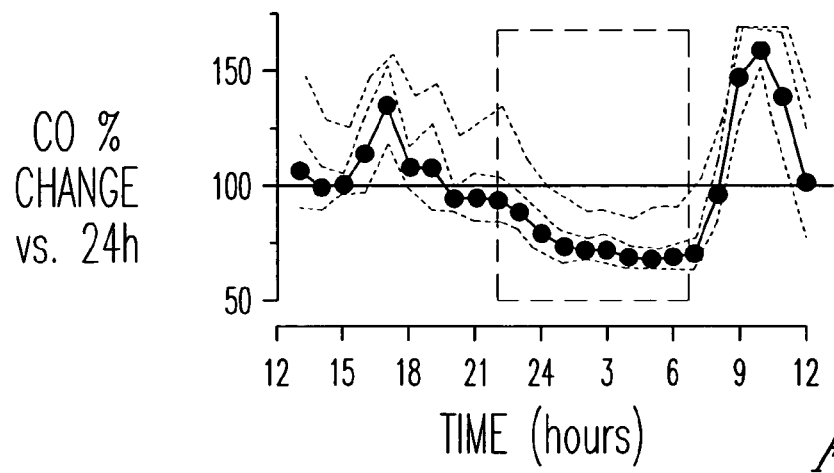
Figure 21E:
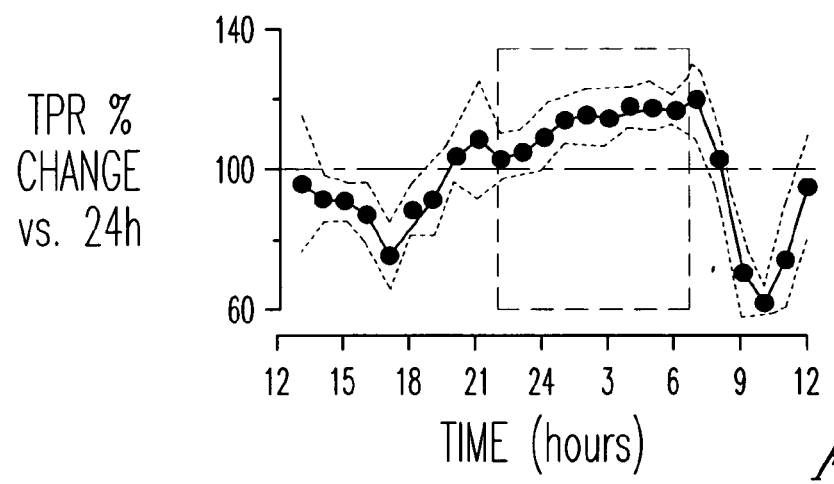

FIGS. 21A-21E illustrate circadian rhythm. FIG. 21A illustrates the circadian rhythm associated with mean arterial pressure for 24 hours from noon to noon; FIG. 21B illustrates the circadian rhythm associated with heart rate for 24 hours from noon to noon; FIG. 21C illustrates the circadian rhythm associated with percent change of stroke volume (SV %) for 24 hours from noon to noon; FIG. 21D illustrates the circadian rhythm associated with the percent change of cardiac output (CO) for 24 hours from noon to noon; and FIG. 21E illustrates the circadian rhythm associated with percent change of total peripheral resistance (TPR %), an index of vasodilation, for 24 hours from noon to noon. Various embodiments graph absolute values, and various embodiments graph percent values. In these figures, the shaded portion represents night hours from about 10 PM to 7 AM, and thus represents rest or sleep times. Referring to FIGS. 21A and 21B, for example, it is evident that both the mean arterial pressure and the heart rate are lowered during periods of rest. A higher blood pressure and heart rate can adversely affect rest. Additionally, a lower blood pressure and heart rate during the day can adversely affect a person's level of energy.

Various embodiments of the present subject matter modulate baroreflex stimulation using a pre-programmed template intended to match the circadian rhythm for a number of subjects. Various embodiments of the present subject matter generate a template customized to match a subject.

Figure 22:
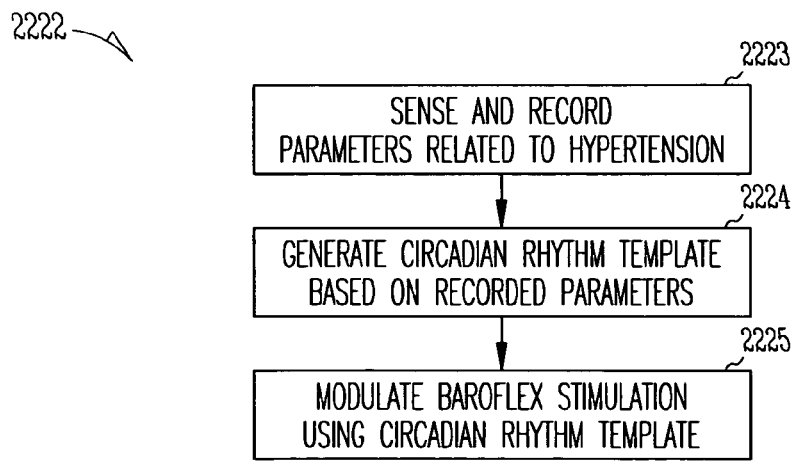
FIG. 22 illustrates a method for modulating baroreceptor stimulation based on circadian rhythm, according to various embodiments of the present subject matter.

FIG. 22 illustrates a method for modulating baroreceptor stimulation based on circadian rhythm, according to various embodiments of the present subject matter, using a customized circadian rhythm template. The illustrated method 2222 senses and records parameters related to hypertension at 2223. Examples of such parameters include heart rate and mean arterial pressure. At 2224, a circadian rhythm template is generated based on these recorded parameters. At 2225, the baroreflex stimulation is modulated using the circadian rhythm template generated in 2224.

Modulation of Baroreflex Stimulation to Provide Desired Cardiac Output

An aspect of the present subject matter relates to an implantable medical device that provides NS therapy to lower systemic blood pressure by stimulating the baroreflex, and further provides cardiac pacing therapy using a cardiac pacing lead for rate control. Baroreflex stimulation and cardiac pacing occurs in tandem, allowing blood pressure to be lowered without sacrificing cardiac output.

According to various embodiments, a baroreflex stimulator communicates with a separate implantable CRM device, and uses the existing pacing lead. In various embodiments, baroreflex stimulation occurs through baroreceptors in the pulmonary artery, carotid sinus, or aortic arch with an electrode placed in or adjacent to the vessel wall. In various embodiments, afferent nerves such as the aortic nerve, carotid sinus nerve, or vagus nerve are stimulated directly with a cuff electrode.

Baroreflex stimulation quickly results in vasodilation, and decreases systemic blood pressure. To compensate for the concurrent decrease in cardiac output, the pacing rate is increased during baroreflex stimulation. The present subject matter allows blood pressure to be gradually lowered through baroreflex stimulation while avoiding the drop in cardiac output that otherwise accompanies such stimulation by combining baroreflex stimulation with cardiac pacing, allowing an implantable device to maintain cardiac output during blood pressure control.

Figure 23A:
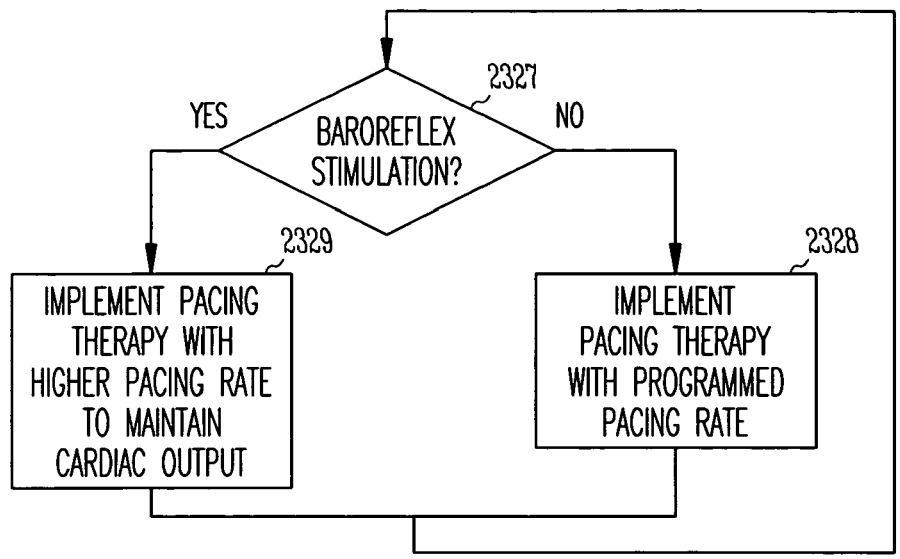
FIG. 23A-B illustrate methods for modulating baroreceptor stimulation based on a cardiac output parameter, according to various embodiments of the present subject matter.
Figure 23B:
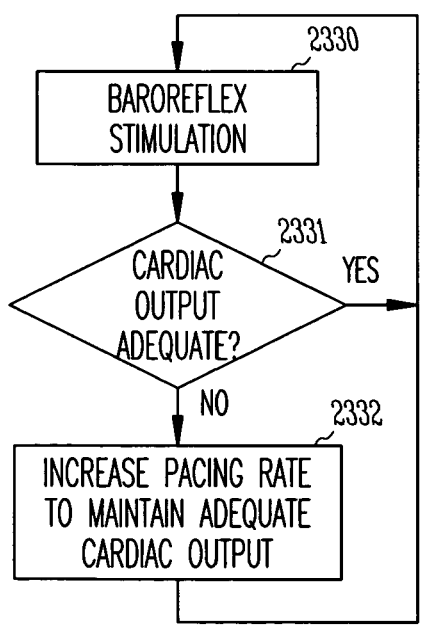

FIG. 23A-B illustrate methods for modulating baroreceptor stimulation based on a cardiac output parameter, according to various embodiments of the present subject matter. FIG. 23A illustrates one embodiment for modulating baroreceptor stimulation based on a cardiac output parameter. In the illustrated process 2326A, it is determined whether baroreflex stimulation is being applied at 2327. If baroreflex stimulation is not being applied, the present subject matter implements the appropriate pacing therapy, if any, at 2328 with the appropriate pacing rate. If baroreflex stimulation is not being applied, the present subject matter implements a pacing therapy at 2329 with a higher pacing rate to maintain cardiac output.

FIG. 23B illustrates one embodiment for modulating baroreceptor stimulation based on a cardiac output parameter. In the illustrated process 2326B, baroreflex stimulation is applied at 2330, and it is determined whether the cardiac output is adequate at 2331. Upon determining that the cardiac output is not adequate, the pacing rate is increased at 2332 to maintain adequate cardiac output.

According to various embodiments, an existing pacing rate is increased by a predetermined factor during baroreflex stimulation to maintain cardiac output. In various embodiments, a pacing rate is initiated during baroreflex stimulation to maintain cardiac output. Modulating baroreflex stimulation to provide desired cardiac output can be implemented with atrial and ventricular rate control, AV delay control, resynchronization, and multisite stimulation. Alternatively, the stroke volume may be monitored by right ventricular impedance using electrodes within the right ventricular cavity or by left ventricular impedance using electrodes within or spanning the left ventricular cavity, and the pacing rate may be increased using application of neural stimulation to maintain a fixed cardiac output.

Modulation of Baroreflex Stimulation to Remodel Stiffening Process

Aspects of the present subject matter involve a method for baroreflex stimulation, used by an implantable NS device, to lower systemic blood pressure in patients with refractory hypertension. A baroreflex stimulation algorithm gradually increases baroreflex stimulation to slowly adjust blood pressure towards a programmable target. This algorithm prevents the central nervous system from adapting to a constant increased level of baroreflex stimulation, which ordinarily attenuates the pressure-lowering effect. In addition, the gradual nature of the blood pressure change allows the patient to better tolerate the therapy, without abrupt changes in systemic blood pressure and cardiac output.

The present subject matter provides a specific algorithm or process designed to prevent central nervous system adaptation to increased baroreflex stimulation, to slowly decrease blood pressure levels with time to enable for the reversion of the arterial stiffening process triggered by the previous hypertensive state present in the patient, and to prevent cardiac output decreases during baroreceptor stimulation. It is expected that, with time, the arterial system reverse remodels the stiffening process that was started by the previously present hypertension. The slow and progressive lowering of the mean/median blood pressure enables the slow reversion of this stiffening process through the reverse remodeling. Blood pressure is reduced without compromising cardiac output in the process, thus avoiding undesired patient symptoms.

In various embodiments, the device stimulates baroreceptors in the pulmonary artery, carotid sinus, or aortic arch with an electrode placed in or adjacent to the vessel wall. In various embodiments afferent nerves such as the aortic nerve, carotid sinus nerve, or vagus nerve are stimulated directly with a cuff electrode. The stimulated baroreflex quickly results in vasodilation, and a decrease in systemic blood pressure. However, rather than stimulating the baroreflex at a constant, elevated level, the device of the present subject matter initially stimulates at a slightly increased level, and then gradually increases the stimulation over a period of weeks or months, for example. The rate of change is determined by the device based on current and target arterial pressure. In various embodiments, the system determines the rate of change based on direct or indirect measurements of cardiac output, to ensure that the decrease in pressure is not occurring at the expense of a decreased cardiac output. In various embodiments, the rate of baroreflex stimulation is not constant but has a white noise type distribution to more closely mimic the nerve traffic distribution. By mimicking the nerve traffic distribution, it is expected that the baroreflex is more responsive to the stimulation, thus lowering the threshold for stimulating the baroreflex.

Figure 24:
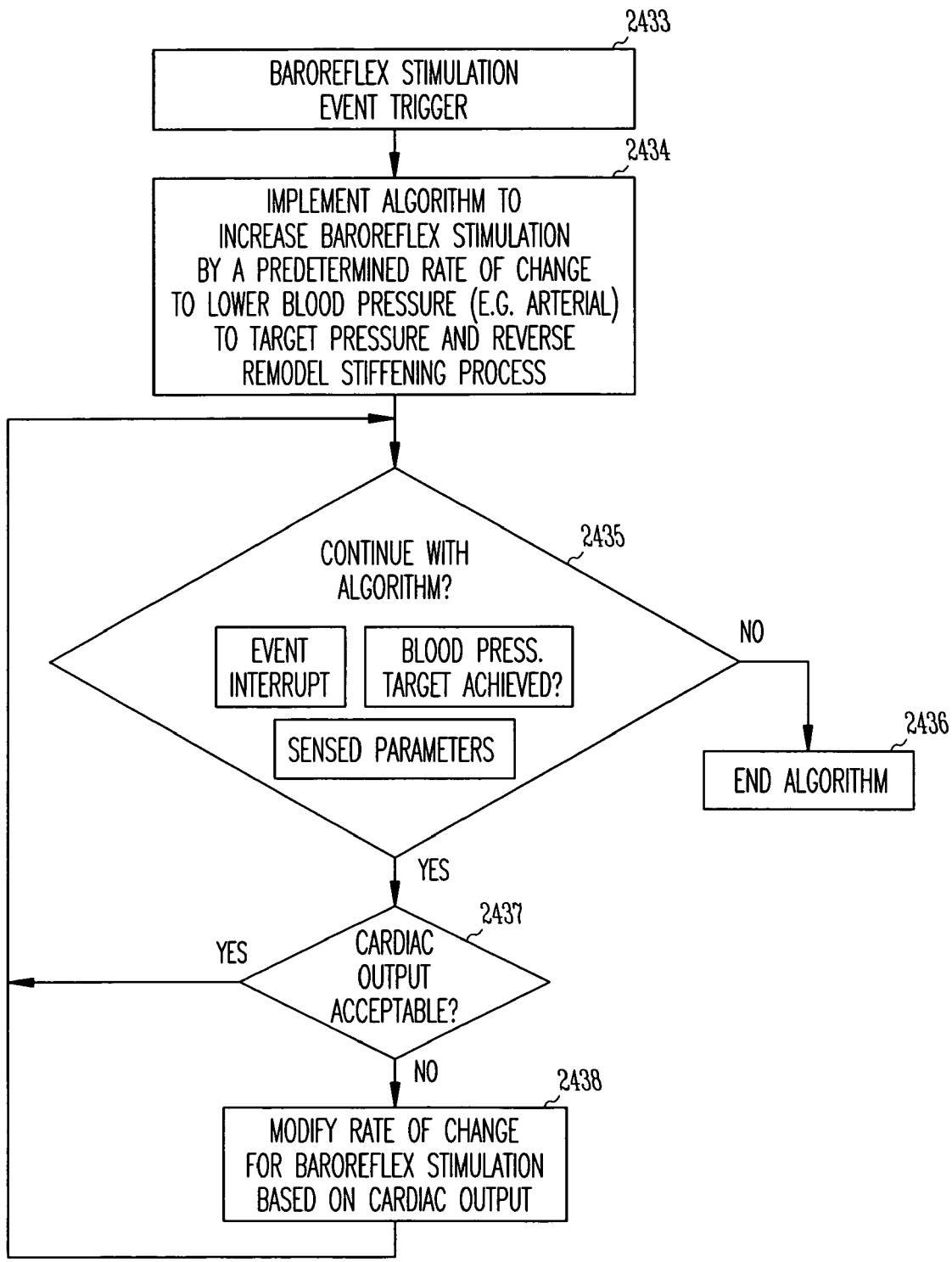
FIG. 24 illustrates a method for modulating baroreceptor stimulation to reverse remodel stiffening, according to various embodiments of the present subject matter.

FIG. 24 illustrates a method for modulating baroreceptor stimulation to reverse remodel stiffening, according to various embodiments of the present subject matter. A baroreflex event trigger occurs at 2433. This trigger includes any event which initiates baroreflex stimulation, including the activation of an AHT device. At 2434, an algorithm is implemented to increase baroreflex stimulation by a predetermined rate of change to gradually lower the blood pressure to a target pressure in order to reverse remodel the stiffening process. At 2435, it is determined whether to continue with the baroreflex stimulation algorithm. The algorithm may be discontinued at 2436 based on an event interrupt, sensed parameters, and/or reaching the target blood pressure, for example. At 2437, it is determined whether the cardiac output is acceptable. If the cardiac output in not acceptable, at 2438 the rate of change for the baroreflex stimulate is modified based on the cardiac output.

Baroreflex Stimulation to Treat Myocardial Infarction

Following a myocardial infarction, myocytes in the infarcted region die and are replaced by scar tissue, which has different mechanical and elastic properties from functional myocardium. Over time, this infarcted area can thin and expand, causing a redistribution of myocardial stresses over the entire heart. Eventually, this process leads to impaired mechanical function in the highly stressed regions and heart failure. The highly stressed regions are referred to as being heavily "loaded" and a reduction in stress is termed "unloading." A device to treat acute myocardial infarction to prevent or reduce myocardial damage is desirable.

An aspect of the present subject matter relates to an implantable device that monitors cardiac electrical activity. Upon detection of a myocardial infarction, the device electrically stimulates the baroreflex, by stimulating baroreceptors in or adjacent to the vessel walls and/or by directly stimulating pressure-sensitive nerves. Increased baroreflex stimulation compensates for reduced baroreflex sensitivity, and improves the clinical outcome in patients following a myocardial infarction. An implantable device (for example, a CRM device) monitors cardiac electrical activity. Upon detection of a myocardial infarction, the device stimulates the baroreflex. Some embodiments of the device stimulate baroreceptors in the pulmonary artery, carotid sinus, or aortic arch with an electrode placed in or adjacent to the vessel wall. In various embodiments, afferent nerves such as the aortic nerve are stimulated directly with a cuff electrode, or with a lead intravenously placed near the afferent nerve. Afferent nerves such as the carotid sinus nerve or vagus nerve are stimulated directly with a cuff electrode, or with a lead intravenously placed near the afferent nerve. In various embodiments, a cardiac fat pad is stimulated using an electrode screwed into the fat pad, or a lead intravenously fed into a vessel or chamber proximate to the fat pad.

Baroreflex stimulation quickly results in vasodilation, and a decrease in systemic blood pressure. This compensates for reduced baroreflex sensitivity and reduces myocardial infarction. According to various embodiments, systemic blood pressure, or a surrogate parameter, are monitored during baroreflex stimulation to insure that an appropriate level of stimulation is delivered. Some aspects and embodiments of the present subject matter provides baroreflex stimulation to prevent ischemic damage following myocardial infarction.

Figure 25A:
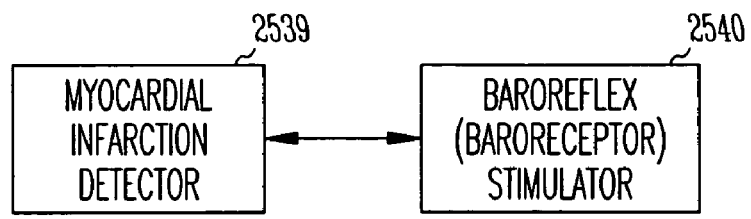
FIGS. 25A-25B illustrate a system and method to detect myocardial infarction and perform baropacing in response to the detected myocardial infarction, according to various embodiments of the present subject matter.
Figure 25B:
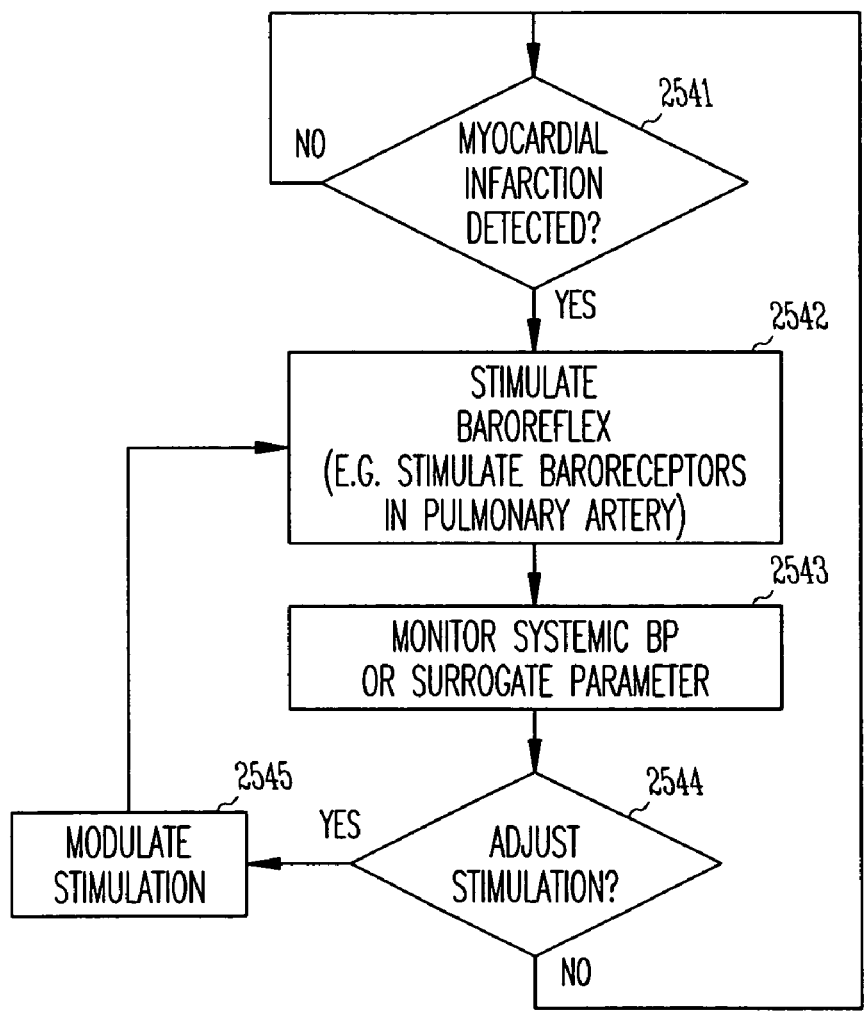

FIGS. 25A-25B illustrate a system and method to detect myocardial infarction and perform baropacing in response to the detected myocardial infarction, according to various embodiments of the present subject matter. FIG. 25A illustrates a system that includes a myocardial infarction detector 2539 and a baroreflex or baroreceptor stimulator 2540. A myocardial infarction can be detected using an electrocardiogram, for example. For example, a template can be compared to the electrocardiogram to determine a myocardial infarction. Another example detects changes in the ST segment elevation to detect myocardial infarction. In various embodiments, the detector 2539 and stimulator 2540 are integrated into a single implantable device such as in an AHT device or a CRM device, for example. In various embodiments, the detector 2539 and stimulator 2540 are implemented in separate implantable devices that are adapted to communicate with each other.

FIG. 25B illustrates a method to detect myocardial infarction and perform baropacing in response to the detected myocardial infarction, according to various embodiments of the present subject matter. At 2541, it is determined whether a myocardial infarction has occurred. Upon determining that a myocardial infarction has occurred, the baroreflex is stimulated at 2542. For example, in various embodiments, the baroreceptors in and around the pulmonary artery are stimulated using a lead fed through the right atrium and the pulmonary valve and into the pulmonary artery. Other embodiments stimulate other baroreceptor sites and pressure sensitive nerves. Some embodiments monitor the systemic blood pressure or a surrogate parameter at 2543, and determines at 2544 if the stimulation should be adjusted based on this monitoring. If the stimulation is to be adjusted, the baroreflex stimulation is modulated at 2545. Examples of modulation include changing the amplitude, frequency, burst frequency and/or waveform of the stimulation.

Neural stimulation, such as baroreflex stimulation, can be used to unload after a myocardial infarction. Various embodiments use an acute myocardial infraction detection sensor, such as an ischemia sensor, within a feedback control system of an NS device. However, a myocardial infraction detection sensor is not required. For example, a stimulation lead can be implanted after a myocardial infarction. In various embodiments, the stimulation lead is implanted through the right atrium and into the pulmonary artery to stimulate baroreceptors in and around the pulmonary artery. Various embodiments implant stimulation cuffs or leads to stimulate afferent nerves, electrode screws or leads to stimulate cardiac fat pads, and leads to stimulate other baroreceptors as provided elsewhere in this disclosure.

Electrical pre-excitation of a heavily loaded region will reduce loading on this region. This pre-excitation may significantly reduce cardiac output resulting in sympathetic activation and an increase in global stress, ultimately leading to deleterious remodeling of the heart. This process may be circumvented by increased neural stimulation to reduce the impact of this reflex. Thus, activation of the parasympathetic nervous system during pre-excitation may prevent the undesirable side-effects of unloading by electrical pre-excitation.

One of ordinary skill in the art will understand that, the modules and other circuitry shown and described herein can be implemented using software, hardware, and combinations of software and hardware. As such, the term module is intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. For example, various embodiments combine two or more of the illustrated processes. Two or more sensed parameters can be combined into a composite parameter used to provide a desired neural stimulation (NS) or anti-hypertension (AHT) therapy. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description.

The scope of the present subject matter should be determined with reference to the appended claims, along with the full scope of equivalents to which such claims are entitled.

What is claimed is:

1. A baroreflex stimulator for delivering baroreflex therapy that follows an intrinsic circadian rhythm, including:
   a sensor adapted to sense blood pressure;
   a pulse generator operationally connected to the sensor and adapted to deliver a baroreflex stimulation therapy using a baroreflex stimulation signal to provide a target blood pressure;
   a circadian rhythm template storage with a circadian rhythm template stored therein, wherein the template reflects the intrinsic cardiac rhythm by reflecting natural fluctuations in a parameter related to hypertension during a day, and
   a modulator operationally connected to the pulse generator and to the circadian rhythm template storage, the modulator configured to change the target blood pressure to mimic natural blood pressure fluctuations during the day using the circadian rhythm template,
   wherein the modulator is configured to follow the circadian rhythm template to adjust the target blood pressure to mimic natural blood pressure fluctuations during the day, and the pulse generator uses the sensed blood pressure as feedback for adjusting the baroreflex therapy to provide the target blood pressure, as adjusted by the modulator, to mimic natural blood pressure fluctuations during the day.

2. The stimulator of claim 1, wherein the baroreflex stimulation signal has an amplitude, and the modulator includes a modulator to modulate the amplitude based on the circadian rhythm template.

3. The stimulator of claim 1, wherein the baroreflex signal has a frequency, and the modulator includes a modulator to modulate the frequency based on the circadian rhythm template.

4. The stimulator of claim 1, wherein the baroreflex signal has a burst frequency, and the modulator includes a modulator to modulate the burst frequency based on the circadian rhythm template.

5. The stimulator of claim 1, further comprising a waveform generator to produce baroreceptor signals of a desired morphology, wherein the modulator includes a modulator to change the morphology of the baroreflex stimulation signal based on the circadian rhythm template.

6. The stimulator of claim 1, wherein the circadian rhythm template storage is programmed to store a circadian rhythm template that reflects natural fluctuations in the parameter related to hypertension during the day for a number of subjects.

7. The stimulator of claim 1, wherein the circadian rhythm template memory is programmed to store a patient-specific circadian rhythm template.

8. The stimulator of claim 1, wherein the circadian rhythm template includes a mean arterial pressure template.

9. The stimulator of claim 1, wherein the circadian rhythm template includes a heart rate template.

10. The stimulator of claim 1, wherein the circadian rhythm template includes a stroke volume template.

11. The stimulator of claim 1, wherein the circadian rhythm template includes a cardiac output template.

12. The stimulator of claim 1, wherein the circadian rhythm template includes a total peripheral resistance template.

13. The stimulator of claim 1, wherein the stimulator is implantable, the stimulator further comprising a lead adapted to be electrically connected to the pulse generator and to be fed through a right ventricle and into a pulmonary artery, the lead including an electrode to be positioned in the pulmonary artery and adapted to deliver the baroreflex stimulation signal to a baroreceptor site in the pulmonary artery.

14. The stimulator of claim 1, further comprising an intravascularly-fed electrode adapted to transvascularly stimulate an afferent nerve using the baroreflex stimulation signal.

15. The stimulator of claim 1, further comprising a nerve cuff electrode adapted to stimulate an afferent nerve using the baroreflex stimulation signal.

16. The stimulator of claim 1, further comprising an electrode adapted to stimulate baroreceptors in a vessel wall using the baroreflex stimulation signal.

17. A baroreflex stimulator for delivering baroreflex therapy that follows an intrinsic circadian rhythm, comprising:
  a sensor adapted to sense blood pressure;
  a pulse generator connected to the sensor and adapted to deliver a baroreflex stimulation therapy using a baroreflex stimulation signal to provide a target blood pressure;
  a circadian rhythm template storage with a circadian rhythm template stored therein, wherein the template reflects the intrinsic cardiac rhythm by reflecting natural fluctuations in a parameter related to hypertension during a day, and
  means for changing the target blood pressure to follow the circadian rhythm template and mimic natural blood pressure fluctuations during the day.

18. The stimulator of claim 17, wherein the circadian rhythm template reflects natural fluctuations in the parameter related to hypertension during the day for a number of subjects.

19. The stimulator of claim 17, wherein the circadian rhythm template includes a patient-specific circadian rhythm template.

20. The stimulator of claim 17, wherein the circadian rhythm template includes a mean arterial pressure template.

21. The stimulator of claim 17, wherein the circadian rhythm template includes a heart rate template.

22. The stimulator of claim 17, wherein the circadian rhythm template includes a stroke volume template.

23. The stimulator of claim 17, wherein the circadian rhythm template includes a cardiac output template.

24. The stimulator of claim 17, wherein the circadian rhythm template includes a total peripheral resistance template.

25. The stimulator of claim 17, wherein the baroreflex stimulation signal has an amplitude, and the means for modulating the baroreflex stimulation signal based on a circadian rhythm template includes means for modulating the amplitude of the baroreflex stimulation signal based on a circadian rhythm template.

26. The stimulator of claim 17, wherein the baroreflex signal has a frequency, and the means for modulating the baroreflex stimulation signal based on a circadian rhythm template includes means for modulating the frequency of the baroreflex stimulation signal based on a circadian rhythm template.

27. The stimulator of claim 17, wherein the baroreflex signal has a burst frequency, and the means for modulating the baroreflex stimulation signal based on a circadian rhythm template includes means for modulating the burst frequency of the baroreflex stimulation signal based on a circadian rhythm template.

28. The stimulator of claim 17, wherein the baroreflex signal has a waveform, and the means for modulating the baroreflex stimulation signal based on a circadian rhythm template includes means for changing a waveform of the baroreflex stimulation signal based on a circadian rhythm template.

* * * * *

UNITED STATES PATENT AND TRADEMARK OFFICE
CERTIFICATE OF CORRECTION

PATENT NO. : 7,706,884 B2  Page 1 of 1
APPLICATION NO. : 10/746844
DATED : April 27, 2010
INVENTOR(S) : Imad Libbus It is certified that error appears in the above-identified patent and that said Letters Patent is hereby corrected as shown below:

In column 1, line 23, delete "10/746,845,filed" and insert -- 10/746,845, filed --, therefor.

In column 6, lines 28-29, after "lead positioned" delete "lead positioned".

Signed and Sealed this

Twenty-third Day of November, 2010

David J. Kappos
*Director of the United States Patent and Trademark Office*